United States Patent
Autzen et al.

(10) Patent No.: US 9,446,088 B2
(45) Date of Patent: Sep. 20, 2016

(54) **PREPARATION AND USE OF A PLANT EXTRACT FROM *SOLANUM GLAUCOPHYLLUM* WITH AN ENRICHED CONTENT OF 1,25 DIHYDROXYVITAMIN D3 GLYCOSIDES AND QUERCETIN GLYCOSIDES**

(71) Applicant: HERBONIS AG, Basel (CH)

(72) Inventors: Sabrina Autzen, Reutlingen (DE); Heinrich Bachmann, Wintersingen (CH)

(73) Assignee: Herbonis AG, Basel (CH)

( * ) Notice: Subject to any disclaimer, the term of this patent is extended or adjusted under 35 U.S.C. 154(b) by 530 days.

(21) Appl. No.: 13/919,560

(22) Filed: Jun. 17, 2013

(65) Prior Publication Data
US 2013/0280351 A1 Oct. 24, 2013

Related U.S. Application Data

(62) Division of application No. 12/988,598, filed as application No. PCT/EP2008/003191 on Apr. 21, 2008, now Pat. No. 8,465,781.

(51) Int. Cl.
*A61K 36/81* (2006.01)

(52) U.S. Cl.
CPC .................................... *A61K 36/81* (2013.01)

(58) Field of Classification Search
None
See application file for complete search history.

(56) References Cited

PUBLICATIONS von Rosenberg (Journal of Steroid Biochemistry and Molecular Biology, (Mar. 2007), vol. 103, pp. 596-600).*

* cited by examiner

*Primary Examiner* — Susan Hoffman
(74) *Attorney, Agent, or Firm* — K&L Gates LLP

(57) ABSTRACT

The present invention relates to the preparation of an enriched and equilibrated plant extract from *Solanum glaucophyllum* with an enriched content of 1,25-dihydroxyvitamin $D_3$, glycosides and flavonols, particularly quercetin glycosides. The present invention particularly describes a method for preparation of such a plant extract either in industrial or in laboratory scale. The present invention furthermore describes the use of such a plant extract or similar (synthetic) compositions for the prevention and treatment of bone mass reduction-related diseases, such as Osteopenia or Osteoporosis, for the prevention and treatment of Tibial Dyschondroplasis, preferably in poultry, for the treatment of milk fever, and is a dietary supplement for human and veterinary use.

12 Claims, 9 Drawing Sheets

PREPARATION AND USE OF A PLANT EXTRACT FROM SOLANUM GLAUCOPHYLLUM WITH AN ENRICHED CONTENT OF 1,25 DIHYDROXYVITAMIN D3 GLYCOSIDES AND QUERCETIN GLYCOSIDES

PRIORITY CLAIM

This application is a divisional of U.S. application Ser. No. 12/988,598, filed Oct. 19, 2010, now U.S. Pat. No. 8,465,781, which is a National Stage of International Application No. PCT/EP08/003191, filed on Apr. 21, 2008 the entire contents of which are expressly incorporated herein by reference thereto.

FIELD OF THE INVENTION

The present invention relates to the preparation of an enriched and equilibrated plant extract from *Solanum glaucophyllum* with an enriched content of 1,25-dihydroxyvitamin $D_3$ glycosides and flavonols, particularly quercetin glycosides. The present invention particularly describes a method for preparation of such a plant extract either in industrial or in laboratory scale. The present invention furthermore describes the use of such a plant extract or similar (synthetic) compositions for the prevention and treatment of bone mass reduction-related diseases, such as Osteopenia or Osteoporosis, for the prevention and treatment of Tibial Dyschondroplasia, preferably in poultry, for the treatment of milk fever, and as a dietary supplement for human or veterinary use.

BACKGROUND

Healthy bones are in a delicate balance of bone resorbing and bone forming processes in order to adapt the skeleton to the changing demands during the whole life span of an individual. This allows the skeleton to grow during childhood, as visualized by the growing skull where minerals are deposited on the outer side and bone is resorbed on the inner side giving space for the growing brain. During adulthood, bones can reinforce themselves for the adaption to loads when performing sports or carrying heavy weights. Bone remodeling is a process with a typical sequence: bone-resorbing osteoclasts dock on the surface of a distinct area and start resorbing bone material. As a result, lacunas or pits are formed. Onto such pits, bone-forming osteoblasts append and these cells deposit new bone material. At the end of such a cycle a region with a stronger bone structure remains. However, in older age or in females after menopause the equilibrium is shifted towards a net bone loss. Bone loss occurs also during long bed rest or under conditions of reduced gravity. As FIG. 1 illustrates, bone mass peaks in mid-age and then declines slowly. In women at risk accelerated bone loss occurs after menopause when estrogen hormone production ceases. Such bone loss is typically diagnosed as Osteoporosis or as Osteopenia (the milder preceding form), wherein the disease Osteoporosis has become a major health problem in populations with increasing life expectancies, particularly in western civilizations.

Not only humans, but also animals suffer from diseases of impaired bone formation both in older age or in young animals during periods of intensive growth. As an example, in animals, particularly in rapidly growing and food producing animals, such as poultry, leg weakness and, as one consequence, Tibial Dyschondroplasia (TD), is a major problem leading to losses and inferior meat quality. Also, due to reasons of animal welfare, the problem of Tibial Dyschondroplasia has to be avoided (see publication Tibial Dyschondroplasia, a Poultry Leg Problem. Rath NC, USDA/ARS, Poultry Production and Product Safety Research, Poultry Science Center, University of Arkansas, USA (Sep. 4, 2003)). Furthermore, laying hens have a massive turnover of calcium because of their eggshell production. Every day, approximately one tenth of the animals' calcium pool has to be taken up from nutrition, stored into the bones and mobilized within a few hours during production of the shell around the egg. Suboptimal supply of Vitamin D can, therefore, also lead to osteoporosis in laying hens.

Many approaches have been suggested and are pursued to prevent age-related and post-menopausal bone loss, wherein e.g. physical training and pharmaceutical treatment are the methods of choice for osteoporosis therapy. Today pharmaceutical treatment/drug treatment typically follows a therapeutic or curative approach, wherein therapy is started when a pathological condition has already been diagnosed, i.e. when bone mass or bone density has fallen under a certain minimum level of necessary bone mass or bone density, or, in the worst case, when a fracture has already occurred. Thus, prevention of an under-run of a minimum of necessary bone mass or bone density would be more preferable to therapy, but should start when bone density is still on a high level and is to be carried out for a long time, e.g. as illustrated in FIG. 1. Thereby, treatments which support physiological mechanisms and which are of natural origin may be a valuable alternative to curative treatment with synthetic drugs.

As of today, anti-osteoporotic drugs typically can be classified according to their mode of action into anti-resorptive agents, anabolics or steroid hormones, bone-forming agents and others, respectively. Alternatively or additionally, anti-osteoporotic drugs may be classified according to their chemical structures, which typically follow one of the above modes of action. Known anti-osteoporotic drugs include e.g. bisphosphonate groups, synthetic estrogens, Vitamin D and its metabolites, etc.

Today most prescribed drugs belong to the bisphosphonate group, acting on the bone resorbing osteoclasts and thereby reducing bone resorption (see e.g. Fleisch H. et al., Endocrine Reviews (1998)19(1): 80-100 Bisphosphonates: Mechanisms of Action). A disadvantage of treatment with drugs of the bisphosphonate group is the blockage of bone-turnover and thus a reduction of bone remodeling.

As evidenced by the strong loss of bone mass after menopause, female sex hormones also possess a strong effect on bone. Therefore, hormone replacement therapy with synthetic estrogens may represent an effective Osteoporosis treatment. Such treatment, however, limited to females and is no longer recommended today since a large clinical study showed an increased incidence of breast cancer as an adverse reaction.

A further, more physiological and thus more promising approach is the support of the Calcium regulation and thus of the natural bone mineral household of the patient to be treated, either as a prevention or as a therapy for the above diseases.

There are many factors, which are involved in Calcium regulation and the natural bone mineral household. Agents acting on Calcium homeostasis include e.g. hormones, such as the hormones calcitonin or parathyroid hormone and synthetic derivatives thereof. Such peptide hormones, however, cannot be administered orally, but need to be administered by injection or as a nasal spray, and thus do not allow an easy administration of the drugs to a patient in need thereof.

The most important factor of the Calcium regulation in animals and humans, including the natural bone mineral household, involves Calcium, typically in the form of a preferably soluble salt or as $Ca^{2+}$. Additionally to the above, Calcium also represents a key agent in intra-cellular signaling, nerve impulse transmission and muscle contraction (Cashman et al., Novartis Found Symp. 2007, 282:123-38, discussion 138-42, 212-8; and Parfitt A M. Bone. 1987, 8 Suppl. 1: S1-8). The insufficient provision of Calcium to the human or animal body may thus lead to concentrations resulting in an under-run of a minimum of necessary bone mass or bone density. On the other hand, without an effective regulation, the content of Calcium in the human or animal body may reach too high concentrations which interfere with intra-cellular signaling, nerve impulse transmission and muscle contraction, or which may lead to toxic side effects. Therefore, in all warm-blooded animals, a tight regulation system prevents the body from toxic calcium concentrations.

A further main component of Calcium regulation in the natural bone mineral household is Vitamin D. Vitamin D is an essential nutrient for optimal bone development as seen in the prevention and healing of rickets, wherein natural and non-natural derivatives of Vitamin D metabolites are known to be used. However, naturally occurring Vitamin D in the form of cholecalciferol (Vitamin $D_3$) or ergocalciferol (Vitamin $D_2$) is biologically not active. Accordingly, naturally occurring Vitamin D is not able to cure slowly developing bone diseases such as Osteoporosis as has been stated in a consensus conference (Osteoporosis Prevention, Diagnosis, and Therapy. NIH Consens Statement Online 2000 Mar. 27-29; 17(1): 1-36.). This is due to the fact that naturally occurring Vitamin D requires two conversion steps to be active, whereby the second step is tightly regulated. According to a first step, after formation in the skin or uptake by ingestion, cholecalciferol (Vitamin $D_3$) is converted in the liver of man and animal into its storage form 25-hydroxyvitamin D3 (also abbreviated as $25(OH)D_3$). A full Vitamin $D_3$ store protects a person for 2 to 3 months against rickets. The storage form is, however, biologically still not active—it needs activation in a second step to the active form of Vitamin $D_3$, i.e. 1,25-dihydroxyvitamin $D_3$ (also abbreviated as $1,25(OH)_2D_3$, Calcitriol), by a kidney enzyme. The active form 1,25-dihydroxyvitamin $D_3$ then activates a gene product in the sensitive tissue. In intestine this is Calbindin, the Calcium-binding protein which is finally capable to take up Calcium from food. The so formed active metabolite 1,25-dihydroxyvitamin $D_3$ furthermore controls Calcium uptake in the intestinal tract and its deposition into and mobilization from bone.

Nevertheless, such natural control mechanisms do most often not lead to a sufficient concentration of the active metabolite in the human or animal body to prevent slow developing bone diseases such as Osteoporosis, particularly in old age, or to prevent other diseases in animals, such as Tibial Dyschondroplasia in poultry.

Since the first discovery of the active principle, various approaches have been started to provide Vitamin $D_3$ for use in medicine, since Vitamin $D_3$ is not abundantly present in nutrition; only marine oils contain substantial amounts. Provision of Vitamin $D_3$ or its metabolites, thus represents an essential basis and also a challenging aspect in efficient therapy of any of the diseases mentioned above. E.g., U.S. Pat. No. 5,508,392 discloses the use of synthetic Vitamin $D_3$ glycosides, Vitamin $D_3$ orthoester glycosides, Vitamin D3 analog glycosides and Vitamin $D_3$ analog orthoester glycosides for the treatment of osteoporosis.

A negative drawback of the administration of Vitamin $D_3$ and its synthetic analogs is the particularly narrow therapeutic window for medication and the risk of hypercalcemia, i.e. an abnormally and toxic high blood concentration of Calcium, which can eventually cause severe damage to soft tissues and kidneys. It may be caused by intoxication with Vitamin $D_3$ (hypervitaminosis $D_3$) due to overdoses at more than 100 times (of) the recommended daily allowance. Such an essential drawback is in particular known for 1,25-Dihydroxyvitamin $D_3$, wherein a small window for medication is open in the range between the effective dose and the dose with beginning toxic side effects, the rate of which is only 2 to 5. As an example, a measurable adverse effect of high doses of 1,25-Dihydroxyvitamin $D_3$ was observed in poultry production leading to a remarkably lower weight gain. However, regardless of the above mentioned drawback, Vitamin $D_3$ and its analogs still appear to be an attractive compound for use in any of the above therapies.

As to whether a therapy is suitable nonetheless also depends on further factors, e.g. the costs for preparing the active compounds used therein. The bottle neck for a cost efficient therapy of diseases as mentioned above using Vitamin $D_3$ or its analogs is, consequently, a cheap provision or preparation of Vitamin D metabolites.

According to one possibility, Vitamin D metabolites may be provided by chemical stereoselective synthesis. Unfortunately, stereoselective synthesis is typically labor intensive and requires many synthesis and purification steps to obtain an enantiomerically enriched or even pure form of a Vitamin $D_3$ or its metabolities. Accordingly, stereoselective synthesis of Vitamin D is expensive and does not allow a cost efficient therapy of any of the diseases mentioned above at the present stage, even though many synthetic Vitamin $D_3$ medicaments are admitted and often prescribed. Furthermore, synthetically produced 1,25-Dihydroxyvitamin $D_3$, administered in high concentrations, has the above mentioned drawback of a particularly narrow therapeutic window for medication and entails the risk of hypercalcemia. Thus, other sources may be preferred for provision of Vitamin $D_3$ or its metabolites.

Still, it was a surprise when plants were discovered that contain Vitamin D metabolites in high amounts. Plants of this type include e.g. species of the family of Solanacea (solanaceous herbs), particularly *Solanum glaucophyllum* (also termed *Solanum malacoxylon* or *Solanum glaucum*), *Solanum torvum, Solanum esuriale, Solanum verbascifolium, Cestrum diurnum*, etc., the species *Nierembergia veichtii*, and species from the family of Gramineae, particularly *Trisetum flavescens*, etc. Intensive research in the last decades furthermore revealed that leaves of tomato plants (*Lycopersicon esculentum* from the family of Solanacea) exhibit a certain amount of Vitamin $D_3$ in the form of $25(OH)D_3$ and $1,25(OH)_2D_3$-glycosides (Prema and Rhagamulu, 1996, Phytochem. 42(3), 617-620). Similarly, potato plants (*Solanum tuberosum*), aubergine plants (*Solanum melongena*) and courgette plants (*Cucurbita pepo* L. ssp. *pepo* convar. *giromontina*) (see e.g. Aburjaj et al. 1998, Phytochem. 46(6), 1005-1018) as well as *Nicotiana glauca* (blue green tobacco from the family of Solanaceae) (Skliar et al, 2000, Plant Science 156, 193-199) showed a considerable amount of Vitamin D. Thus, there are potentially some plants, which may serve as a basis for provision of Vitamin D or its metabolites.

Basis for this discovery was the occurrence of beneficial effects upon feeding animals with leaves or other parts of these plants. Several of these beneficial effects of dried leaves of such calcinogenic plants have been published (see e.g. Boland et al., Plant Science 00, 1-13 (2003)). Also, some applications disclosed the use of extracts from these plants. E.g. U.S. Pat. No. 5,776,461 discloses cosmetic compositions containing phytovitamin D, particularly natural skin care composition containing selected hydroxylated Vitamin D compounds or their glycosides, which are derived from plant sources (phytovitamins D).

One plant with the highest concentrations of Vitamin D turned out to be *Solanum glaucophyllum*. In particular, it has been found that *Solanum glaucophyllum*, earlier known as *Solanum malacoxylon*, contains Vitamin D. In parts of the species *Solanum glaucophyllum* the active component was identified as the Vitamin $D_3$ metabolite 1,25-Dihydroxyvitamin $D_3$ (see e.g. De Vernejou) et al., La Nouvelle Presse medicate, 7, 22, 1941-43 (1978)).

While extensive literature exists on the Vitamin D active components in *Solanum glaucophyllurn*, very little is known on other components of the plant. Solely one publication described the presence of the alkaloid solasodine in the plant (see Jain and Sahoo, Pharmazie (1986) 41:820-821) and one publication described the presence of phenolic compounds; however no quantitative portions of these compounds were given (Rappapport et al., Phytochemistry (1977) 16:1115-6). Apart from its main component 1,25-dihydroxyvitamin $D_3$, in *Solanum glaucophyllum* was found a series of phenolic glycosides by butanol extraction of the plant including hydroquinone, kaempferol and quercetin and the following known glycosides arbutin, O-methylarbutin, isoquercetin, avicutarin, rutin, kaempferol-3-O-rutinoside and isorhamnetin-3-O-rutinoside. A new quercetin trioside, the compound quercetin 3-O-[2G-b-D-apiosyllrutinoside was also found in *Solanum glaucophyllum*. Many of these phenolic compounds are constituents of all plants and no quantitative content was given in the publication of Rappaport et al. (1977, supra). Furthermore, flavonoids, a subclass of plant phenols, are typically discussed as antioxidants, whereas a positive activity in bone formation has not been shown or discussed. Moreover, only for (the plant phenolic sub-class) flavonols (quercetin and kaempferol) an effect on bone cells has been described. For example, recent in vitro experiments indicate an inhibition of osteoclast formation and differentiation of osteoctastic precursor cells by quercetin and rutin. Yamaguchi found a potent inhibitory effect on osteoclastogenesis and bone resorption rather than bone formation in vitro by quercetin and kaempferol (Yamaguchi et al., Mol Cell Biochem. 2007 Jun. 1). On a genomic level quercetin and its glucuronide promote an increase of the mRNA level of bone sialoprotein (Kim et al., J Cell Biochem. 2007 Jun. 1). Other in vitro studies in cells of the osteoctastic lineage confirmed an inhibiting effect on osteoclast differentiation, a critical determinant step in bone resorption, but no positive effect on bone formation was shown (Wattel et al., J Cell Biochem. 2004 May 15; 92(2):285-95).

On a higher level, experiments in ossicle organ cultures (Sziklai and Ribari, Acta Otolaryngol. 1995 March; 1 1 5(2):296-9) and in rat calvarial osteoblast cells (Yang et al., Zhong Yao Cai. 2006 May; 29(5):467-70) also showed an inhibiting effect of quercetin on osteoblastic cells. Furthermore, in two studies with intact animals quercetin was effective in bone mineral metabolism, biomechanical strength and bone structure in streptozutocin-induced diabetic rats (Kanter et al., Cell Biochem Funct. 2007 Jan. 31) and rutin in ovariectomy-induced osteopenia in rats (Horcajada-Molteni et al., J Bone Miner Res. 2000 November; 15(11):2251-8. Comment in: J Bone Miner Res. 2001 May; 16(5):970-1). Nevertheless, even if these compounds have been determined to occur in plants of *Solanum glaucophyllum*, prior art only discusses Vitamin D as sole active principle in the treatment of diseases as mentioned above.

At the time of discovery of the high content of Vitamin D metabolite 1,25-dihydroxyvitamin D3 in *Solanum glaucophyllum*, it has been speculated whether the plant can be used to treat bone diseases in man and animals and the biological activity of the extract has been explored in laboratory animals. Such experiments used Vitamin D-depleted animals in order to prove the Vitamin D activity (see e.g. De Vernejoul. et al., (1978), supra). Azcona (Azcona et al., Zootechnica Intern. February 1982 p. 12-13). Morris (Morris K M L, The Veterinary Record, 101, 502-504 (1977)) found a higher eggshell strength after feeding dry leaves of *Solanum glaucophyllum*. Norrdin (Norrdin at al, Calcified Tissue International (1979) 28(1):239-243) noticed a higher bone mass and breaking strength in chicken bones after application of dry leaves of the same plant. An aqueous leaf extract furthermore showed a higher Vitamin D activity after incubation with rumen fluid of bovines and sheep (Mello and Habermehl, Dtsch Tierarztl Wochenschr. 1992 September; 99(9):371-6). From WO 85/05110 it is also known that extracts from the leaves of the South-American plant *Solanum glaucophyllum* contains 1,25-Dihydroxyvitamin $D_3$ and a water-soluble principle which is different from 1,25-Dihydroxyvitamin $D_3$ and which, upon treatment with rumen fluid, yields 1,25-Dihydroxyvitamin $D_3$ plus a water-soluble carbohydrate In said prior art it is further stated that the water-soluble extract of *Solanum glaucophyllum* has a biological activity which is similar to that of 1,25-Dihydroxyvitamin $D_3$. From the Austrian Patent Specification AT 398 372 B which was published approximately 9 years after WO 85/05110 it can be seen that dried leaves of *Solanum glaucophyllum* indeed have the alleged activity but also the above mentioned known drawback of high toxicity. Later, Cheng et al. (2004) (Cheng et al., Poult Sci. 2004 March; 83(3):406-13.) found improved phosphorus utilization in broiler chickens when fed leaves of *Solanum glaucophyllum*. Furthermore, Foote et al. (2004) (Foote et al., J Anim Sci. 2004 January; 82(1):242-9) found that Vitamin D and its metabolites obtained from plants containing such metabolites can improve meat tenderness when fed before slaughtering. However, all these attempts share the above mentioned known drawback of high toxicity.

Furthermore, dried leaves of the plant were given to patients suffering from hyperthyroidism and kidney insufficiency for up to 7 days. A normalizing effect on plasma calcium was observed (see e.g. Mautalen et al., Calcif Tissue Res. 1977 May; 22 Suppl:534-7; and Herrath et al., Vitamin D, Chemical and Clinical Aspects related to Calcium Metabolism. Pp. 703-708. W. de Gruyter, Berlin, Germany, 1977). Particularly limiting in this case is the application of an unpurified extract of unknown activity, which typically contains toxic alkaloids.

Common to all these trials was additionally that the material used was not characterized and no active component was measured in all experiments. Furthermore, no other than Vitamin D-like effects were described for *Solanum glaucophyllum*.

On the other hand, several papers have been published on attempts to analyze the active principle of *Solanum glaucophyllum* and to prepare plant extracts For example, Peterlik and Wasserman (1975) (see Peterlik and Wasserman, FEBS Letters (1975) 56:16-19) extracted dry leaves with chloroform/methanol mixtures, while Mello and Habermehl (1998) extracted dry plant material with hot water (see Mello and Habermehl, Dtsch Tierarztl Wochenschr. 1998 January; 105(1):25-9). Further purification was performed by chromatography on Sephadex G1 5 and Sephadex LH2O (see Vidal et al., Turrialba (1985) 35:65-70) or by preparative HPLC chromatography on columns with silica and C18-modified silica as stationary phases (Skliar et al., J Steroid Biochem Mol Biol. 1992 December; 43(7):677-82).

The publication of von Rosenberg S. J., 2006 (Rosenberg S. J., 2006, PhD-thesis, Ludwigs-Maximilians-University, Munich, Germany) and the subsequent publication of von Rosenberg S. J. et al. 2007, (Rosenberg S. J. et al., The Journal of Steroid Biochemistry and Molecular Biology, Volume 103, Issues 3-5, March 2007, Pages 596-600) furthermore disclose plant extracts from *Solanum glaucophyllum* and *Trisetum flavescens* for use as food supplement or for human therapy, particularly Osteoporosis. The plant extracts disclosed therein were provided by Herbonis AG, Basel, Switzerland, and have been prepared by aqueous extraction of dried plants (leaves) followed by purification of the extract using high pressure liquid chromatography (HPLC) with Sephadex as a matrix material. The extract solely contained the active Vitamin D metabolite 1,25-Dihydroxyvitamin $D_3$ as active principle.

Even if some laboratory extraction methods have been published in the meantime, none of the above publications likewise discloses a method for extracting and/or purifying a plant extract containing Vitamin D compounds with a sufficiently high, i.e. an industrially applicable, yield. The methods used are convenient to find the active principle 1,25-dihydroxyvitamin $D_3$ but no attempt has been made to optimize yield and minimize toxic by-products. Extractions with pure water or aqueous compositions to separate the free 1,25-dihydroxyvitamin $D_3$ from the bound form have been made, or, chloroform, an itself toxic solvent, was used to isolate the free 1,25-dihydroxyvitamin $D_3$ from the water-soluble components. For the purification of the active principle 1,25-dihydroxyvitamin $D_3$ several methods have been described using column chromatography with silica material or Sephadex gels, but such methods are not feasible for the production of larger quantities of extracts. Particularly, chromatography on silica material gives lower yields of Vitamin D metabolites and thus does not allow production of Vitamin D containing plant extracts in industrial scale, showing a considerable amount of Vitamin D. Furthermore, none of the above applications managed to provide a plant extract, which overcomes at least in part the above drawback of high toxicity when administered in higher concentrations.

SUMMARY

Accordingly, it is an object of the present invention to overcome the above disadvantages and to provide a *Solanum glaucophyllum* extract with an improved tolerance which is obtainable in large quantities in a cost efficient manner, particularly an extract, which does not exhibit the above restrictions due to the toxicity of Vitamin D in higher concentrations.

The present invention provides a solution to the underlying object as shown in the following and by the attached claims.

According to the invention, this urgent need is satisfied by a novel method for the production of an enriched (and equilibrated) plant extract from *Solanum glaucophyllum*, which contains both 1,25-dihydroxyvitamin $D_3$ glycosides and flavonols, particularly quercetin glycosides, in a sufficiently high yield and by a method, which is applicable to industrial scale.

The inventors of the present invention surprisingly found, that plant extracts from *Solanum glaucophyllum*, showing an enriched content of both 1,25-dihydroxyvitamin $D_3$ glycosides and flavonols, particularly quercetin glycosides, do not show the above drawback of high toxicity, ie. Vitamin D metabolites may be administered at much higher concentrations than shown in the art without the risk of hypercalcemia. Additionally, such enriched plant extracts also allow administration of lower concentrations of both 1,25-dihydroxyvitamin $D_3$ glycosides and flavonols, particularly quercetin glycosides, which still lead to a measurable and good effect. In other words, the inventors of the present invention surprisingly found, that a high content of both 1,25-dihydroxyvitamin $D_3$ glycosides and flavonols, particularly quercetin glycosides, in plant extracts derived from *Solanum glaucophyllum*, contrary to extracts known from the art containing only a high content of Vitamin $D_3$ compounds, is capable to significantly open the particularly narrow therapeutic window for medication using Vitamin D metabolites. However, there was no disclosure in the art, which allowed preparation of such an enriched plant extract or a plant extract showing such properties.

Method for Preparation and Purification of an Enriched Plant Extract from *Solanum glaucpphyllum*

According to a first embodiment, the present invention provides a method for preparation and purification of an enriched (and equilibrated) plant extract from *Solanum glaucophyllum* having an enriched content of 1,25-dihydroxyvitamin $D_3$ glycosides and flavonols, particularly quercetin glycosides, wherein the method preferably comprises the following steps:

a) extracting plants or parts thereof from the species *Solanum glaucophyllum* using an alcohol based solvent; and b) purifying the extract obtained according to step a), preferably using the steps:

b1) applying the plant extract obtained according to step a) to a column comprising a non-ionic polymer resin;

b2) optionally washing the column with water and/or an alcohol based solvent as defined herein;

b3) eluting the enriched plant extract from the column; and b4) optionally concentrating and/or drying the enriched plant extract.

According to a extraction step a) of the inventive method for preparation and purification of an enriched plant extract from *Solanum glaucophyllum*, plants or parts thereof from the species *Solanum glaucophyllum* are extracted using an alcohol based solvent, which is superior to the above mentioned methods of the art and by a method, which is applicable to industrial scale. In contrast, published methods are solely focused on analytical tasks and are not feasible for industrial scale. Furthermore, such methods are only designed to obtain pure Vitamin $D_3$ active components. Additionally, such methods are, in part, not suitable for human or veterinarian use due to toxicity of the solvents used therein. As an example, extraction methods for *Solanum glaucophyllum* published in the art based on the use of chloroform-methanol were described as most efficient but are not usable for larger volumes and involve toxic reagents. Furthermore, published extraction methods involving solely water resulted in lower vitamin D activity. According to the own findings of the applicant, an alcohol based solvent surprisingly turned out to provide the best results. Therefore, an alcohol based solvent suitable for extraction step a) of the inventive method for preparation and purification is preferably selected from the group comprising a mixture of water and an alcohol, or an alcohol alone, wherein the alcohol is preferably selected from methanol, ethanol or isopropanol, more preferably from ethanol or methanol. Extraction of plants or parts thereof from the species *Solanum glaucophyllum* according to extraction step a) of the inventive method using other suitable and widely used solvents (e.g. water) is also encompassed herein, even though less favorable for obtaining the optimal composition of plant extract. Even more preferably, the solvent in step a) of the inventive method for preparation and purification of a plant extract from *Solanum glaucophyllum* is selected from an ethanol/water mixture having a ratio (%) of about 100/0 to about 0/100 ethanol/water (v/v), e.g. may be selected from an ethanol/water mixture having a ratio (%) of about 100/0 ethanol/water (v/v), about 95/5 ethanol/water (v/v), about 90/10 ethanol/water (v/v), about 85/15 ethanol/water (v/v), about 80/20 ethanol/water (v/v), about 75/25 ethanol/water (v/v), about 70/30 ethanol/water (v/v), about 65/35 ethanol/water (v/v), about 60/40 ethanol/water (v/v), about 55/45 ethanol/water (v/v), about 50/50 ethanol/water (v/v), about 45/55 ethanol/water (v/v), about 40/60 ethanol/water (v/v), about 35/65 ethanol/water (v/v), about 30/70 ethanol/water (v/v), about 25/75 ethanol/water (v/v), about 20/80 ethanol/water (v/v), about 15/85 ethanol/water (v/v), about 10/90 ethanol/water (v/v), about 5/95 ethanol/water (v/v), or about 0/100 ethanol/water (v/v), or may be selected from a region formed by two of any of the specific values mentioned above. Such mixtures have been found superior in the inventive task to obtain the maximum yield of both desirable components of the inventive enriched plant extract, i.e. both 1,25-dihydroxyvitamin $D_3$ glycosides and flavonols, particularly quercetin glycosides. Most preferably, the solvent in extraction step a) of the inventive method for preparation and purification of an enriched plant extract from *Solanum glaucophyllum* may be selected from an ethanol/water mixture having a ratio (%) of about 80/20 to about 50/50 and/or about 35/65 to about 20/80 ethanol/water (v/v). The particular ratio of ethanol/water (v/v) may further be selected due to the required specific content of 1,25-dihydroxyvitamin $D_3$ glycosides in the enriched plant extract as defined herein. Such particular ratios of ethanol/water (v/v) may be selected by a skilled person dependent on the specific method for extraction and purification, more preferably as defined herein.

Alternatively, but less preferred, the solvent in extraction step a) of the inventive method for preparation and purification of an enriched plant extract from *Solanum glaucophyllum* may be selected from a methanol/water mixture having a methanol/water ratio as described above for the ethanol/water mixture. More preferably, the methanol/water ratio may be selected from a ratio (%) of about 90/10 to about 25/75 methanol/water (v/v), e.g. may be selected from a methanol/water mixture having a ratio (%) of about 90/10 methanol/water (v/v), about 85/15 methanol/water (v/v), about 80/20 methanol/water (v/v), about 75/25 methanol/water (v/v), about 70/30 methanol/water (v/v), about 65/35 methanol/water (v/v), about 60/40 methanol/water (v/v), about 55/45 methanol/water (v/v), about 50/50 methanol/water (v/v), about 45/55 methanol/water (v/v), about 40/60 methanol/water (v/v), about 35/65 methanol/water (v/v), about 30/70 methanol/water (v/v), or about 25/75 methanol/water (v/v), or may be selected from a region formed by two of any of the specific values mentioned above, in particular about 90/10 to about 60/40 and/or about 40/60 to about 25/75 methanol/water (v/v).

According to a further but less preferred alternative, the solvent in extraction step a) of the inventive method for preparation and purification of an enriched plant extract from *Solanum glaucophyllum* may be selected from an isopropanol/water mixture having an isopropanol/water ratio as described above for the ethanol/water mixture or the methanol/water mixture.

The concentration of the (dried) plants or parts thereof from the species *Solanum glaucophyllum* in the alcohol based solvent as defined above may require a specific ratio of the used solvent versus the (total amount of) (dried) plants or parts thereof (drugs) in the solvent, i.e. the solvent/drug ratio (%), which is preferably about 4-40 (v/w), more preferably about 4-30 (v/w) or about 4-25 (v/w), and even more preferably may be dependent on the extraction method used, e.g. about 7-12 or 8-10 (v/w), most preferably about 9 (v/w), e.g. for percolation type extractions; alternatively about 3-7 or 4-6 (v/w), most preferably about 5 (v/w), e.g. for maceration type extractions. In this context percolation type extractions and maceration type extractions are regarded as equivalent alternatives for in extraction step a) of the present inventive method.

The solvent according to extraction step a) of the inventive method for preparation and purification of an enriched plant extract from *Solanum glaucophyllum* may further contain additives. Such additives may be added in order to improve the quality of the obtained extract. In general, such additives may be contained in the solvent according to step a) of the inventive method for preparation and purification in a concentration suitable for the intended purpose, which may be determined by a skilled person according to the specific requirements of the extraction step. Typically, such additives are selected in such a concentration, that the extraction according to step a) is not impaired by these compounds but allows additional stabilization and/or a protective antioxidant effect, etc. Additives in the context of the present invention may include, e.g. antioxidants, such as e.g. ascorbic acid, preferably in a concentration of about 0.01% (w/v) to about 2% (w/v), preferably in a concentration of about 0.05% (w/v) to about 1% (w/v), and most preferably in a concentration of about 0.05% (w/v) to about 0.5% (w/v), or tocopherol or antioxidants of the gallert type (E310, E211 or E312), preferably in a concentration of about 0.02 to about 1% (w/v), more preferably in a concentration of about 0.05% (w/v) to about 0.25% (w/v), etc. Additives may furthermore comprise suitable acids, preferably, organic acids, more preferably plant derived acids or acids occurring in plants, including e.g. acetic acid, sulfuric acid, citric acid, etc., preferably in a concentration of about 0.05% (w/v) to about 1% (w/v), even more preferably in a concentration of about 0.1% (w/v) to about 0.5% (w/v). Any % (w/v) is determined with respect to the entire volume of the solvent used for extraction according to step a). Addition of such acids is preferable to reduce browning reactions during extraction and subsequent steps. Accordingly, the pH value may be adjusted during extraction according to extraction step a) of the inventive method, to a specific pH-value of about 4.0 to about 8.0, more preferably to a specific pH-value of about 5.5 to about 6.5. Adjusting the pH-value may be carried out by adding a suitable amount of a suitable acid, e.g. as defined above, or, if necessary, by a suitable amount of a suitable base, e.g. sodium hydroxide, potassium hydroxide, etc.

The extraction according to step a) of the inventive method for preparation and purification of an enriched plant extract from *Solanum glaucophyllum* may comprise the step of grinding, percolating and/or macerating the plants or parts from the species *Solanum glaucophyllum*, e.g. leaves. The grinding, percolating and/or macerating. may be carried out either in a continuous process or a discontinuous process.

Extraction step a) of the inventive method for preparation and purification of an enriched plant extract from *Solanum glaucophyllum* may be carried out in a temperature range of an ambient temperature to about 85° C., e.g. about 20 or 30° C. to about 85° C., more preferably in a temperature range of about 30° C. to about 70° C., and most preferably in a temperature range of about 40° C. to about 60° C., particularly at a temperature of about 40° C., about 45° C., about 50° C., about 55° C., or about 60° C., more preferably at a temperature of about 50° C., about 55° C. or about 60° C., or within a range formed by any of the afore mentioned values.

The extraction according to step a) of the inventive method for preparation and purification of an enriched plant extract from *Solanum glaucophyllum* may be repeated at least once, preferably 1-2 times, 1-3 times, 1-5 times or more, preferably with about 1 to about 5, 1 to 4, 1 to 3, 1 to 2 or 1 (bed) volume(s) of the same alcohol based solvent used for extraction, in order to increase the yield of the active components to be extracted. The solvents may be then combined after extraction. A suitable choice may be dependent on the extraction method used, e.g. a maceration or a percolation type extraction. When maceration is used as an extraction method, extraction step a) is preferably repeated 1-2 times with about 2 to about 5 (bed) volumes of the same alcohol based solvent as used for the first extraction according to extraction step a). It is to be noted in this context, that, surprisingly, the inventors found that no grinding of the plants or parts thereof is necessary to obtain a good yield during extraction according to step a).

Alternatively or additionally, the extraction according to step a) of the inventive method for preparation and purification of an enriched plant extract from *Solanum glaucophyllum* may be carried out for a specific time interval, wherein the time interval, i.e. the extraction time, may vary from about 1 to about 48, 24, or about 10 hours, preferably from about 6 to about 48 hours, more preferably about 24 hours.

The plant extract obtained according to extraction step a) may be filtered. Filtering may be carried out using methods known in the art. Filtering may occur, e.g. by pumping the solvent through a 40 to 60 pm, preferably a 50 pm mesh width. The extract obtained according to extraction step a) may be filtered continuously, after each extraction step or at the end of all extraction steps according to extraction step a).

The extract obtained according to extraction step a) of the inventive method for preparation and purification of a plant extract from *Solanum glaucophyllum* may be concentrated (prior to or subsequent to filtering) and/or dried using a suitable method. Concentrating and/or drying in the context of extraction step a) as well as in the present invention in general is intended to mean any reduction of moisture or liquid of the plant extract, e.g. after percolating or macerating the plants or parts thereof from the species *Solanum glaucophyllum* according to step a). Such reduction of moisture or liquid of the plant extract, obtained e.g. during extraction step a) may be carried out by concentrating the extract, preferably using conventional concentrating and/or drying means and methods, more preferably using methods, which allow to carefully reduce the moisture or liquid of the enriched plant extract without decomposing its main constituents, particularly 1,25-dihydroxyvitamin $D_3$ glycosides and flavonols, particularly quercetin glycosides. Methods for concentrating (and/or drying) may include, without being limited thereto, e.g., evaporation, e.g. evaporation under vacuum, or distillation of the solvents using smooth temperatures. Drying methods may use an already concentrated extract but may also directly start from a plant extract obtained after extraction (and/or purification). Such drying methods may include, without being limited thereto, e.g., spray-drying, band drying, lyophilizing, etc., particularly, when the (intermediary) plant extract is to be dried to a content of about or near to 100% non-volatile matter.

Preferably, during concentrating or drying of the plant extract according to extraction step a), the organic solvents are removed first, then water is removed until a solution is obtained which contains a specific content (%) of water and a specific content (%) of non-volatile matter. As an example, the plant extract obtained according to extraction step a) may be concentrated or dried until the plant extract contains a content of about 90-80% water and about 10-20% non-volatile matter, a content of about 85-75% water and about 15-25% non-volatile matter, a content of about 80-70% water and about 20-30% non-volatile matter, a content of about 75-65% water and about 25-35% non-volatile matter, a content of about 70-60% water and about 30-40% non-volatile matter, a content of about 65-55% water and about 35-45% non-volatile matter, a content of about 60-50% water and about 40-50% non-volatile matter, a content of about 55-45% water and about 45-55% non-volatile matter, a content of about 50-40% water and about 50-60% non-volatile matter, a content of about 45-35% water and about 55-65% non-volatile matter, a content of about 40-30% water and about 60-70% non-volatile matter, a content of about 35-25% water and about 65-75% non-volatile matter, a content of about 30-20% water and about 70-80% non-volatile matter, a content of about 25-15% water and about 75-85% non-volatile matter, a content of about 20-10% water and about 80-90% non-volatile matter, a content of about 15-5% water and about 85-95% non-volatile matter, or a content of about 10-0% water and about 90-100% non-volatile matter, preferably a content of about 85-75% water and about 15-25% non-volatile matter, a content of about 80-70% water and about 20-30% non-volatile matter, a content of about 75-65% water and about 25-35% non-volatile matter, a content of about 70-60% water and about 30-40% non-volatile matter, a content of about 65-55% water and about 35-45% non-volatile matter, and most preferably a content of about 75-65% water and about 25-35% non-volatile matter, each determined on basis of the total weight the plant extract prior to concentration or drying, e.g. as obtained directly after a percolation or maceration type extraction. Such a concentration and/or drying to a specified content of non-volatile matter allows to equalize the different concentrations of active principles to a specified concentration of the plant extract obtained according to extraction step a), which may be obtained when using different volumes of the above (alternative) solvent(s) for extraction, e.g. when repeating extraction according to step a). Concentrating and/or drying of the plant extract obtained according to step a) to a content of about 100% non-volatile matter additionally allows storing the extract until use for a further process step with a minimum of space required.

Finally, the plant extract obtained according to step a) may be subjected to a heat-/high temperature treatment in order to increase the shelf life of the extract, preferably to allow (longer) storage of the extract. Such a step may occur prior to or subsequent to concentration and/or drying the plant extract obtained according to step a). The heat-/high temperature treatment may be carried out using methods known in the art. More preferably, heat-/high temperature treatment is carried out under gentle conditions, preferably between about 100° C. to about 145° C., e.g. at a minimum of about 100° C., preferably for about 30 to 40 seconds, or at a maximum of about 145° C., preferably for about 2 to 10 seconds, or at any value in between, e.g. about 105° C., 110° C., 115° C., 120° C., 125° C., 130° C., 135° C., or about 140° C.

According to a particularly preferred embodiment, extraction step a) of the inventive method for preparation and purification of an enriched plant extract from *Solanum glaucophyllum* may be carried out in laboratory scale or in industrial scale, wherein laboratory conditions as defined herein may also be transferred to industrial scale.

If carried out in laboratory scale, extraction step a) of the inventive method for preparation and purification typically starts, without being limited thereto, with an amount of plants or parts from the species *Solanum glaucophyllum* in the range of about 0.5 g to about 1000 g, more preferably in a range of about 1 g to about 100 g, and most preferably in the range of about 1 g to about 10 g, wherein the leaves may be ground, percolated or macerated in the alcohol based solvent. The alcohol based solvent may be selected as defined above, more preferably may be selected from an ethanol/water mixture having a ratio (%) of about 80/20 to 20/80, or more preferably 80/20 to 65/35, or alternatively 35/65 to 20/80 ethanol/water (v/v), e.g. may be selected from an ethanol/water mixture having a ratio (%) of about 80/20 ethanol/water (v/v), about 75/25 ethanol/water (v/v), about 70/30 ethanol/water (v/v), about 65/35 ethanol/water (v/v), about 60/40 ethanol/water (v/v), about 55/45 ethanol/water (v/v), about 50/50 ethanol/water (v/v), about 45/55 ethanol/water (v/v), about 40/60 ethanol/water (v/v), about 35/65 ethanol/water (v/v), about 30/70 ethanol/water (v/v), about 25/75 ethanol/water (v/v), or about 20/80 ethanol/water (v/v), or may be selected from a region formed by two of any of these specific values. Furthermore, pH-value and temperatures used during the extraction process in laboratory scale may be selected as defined above in general, wherein preferably such conditions are selected, which lead to an efficacy of extraction of greater than 3 (see below in Table 1, Example 1 A). Preferably, temperatures of about 40° C. to 60° C. may be used, more preferably a temperature of about 50° C. The extraction may be repeated as mentioned above, preferably 1-5 times.

In this context, the efficacy of the extraction according to step a) of the inventive method for preparation and purification of an enriched plant extract from *Solanum glaucophyllum* may be calculated according to the following formula:

$$yf = VDM_{(extract)}[Qu_{(extract)}/1000] \cdot ef$$

VDM=1,25-Dihydroxyvitamin $D_3$ (or a glycoside thereof or a further active Vitamin D compound as defined above)

Qu=quercetin ef: empirical process factor yf: weighed goodness of process whereby the terms [VDM] and [Qu] are calculated per g extract. The factor [ef] weights empirical factors as costs, ecology and quality of the extract (e.g. solubility). As a surprising result of the present invention the efficacy of extraction yf greater than 3 is satisfying and superior to known extraction methods and fulfills the criteria of the present invention. Accordingly, a preferred embodiment of extraction step a) of the present inventive method provides extracts having a value for yf, which is >2, more preferably >2.5, even more preferably >3.

If carried out in industrial scale, extraction step a) of the inventive method for preparation and purification typically starts, without being limited thereto, with an amount of plants or parts from the species *Solanum glaucophyllum* in the range of at least about 1000 g, preferably of at least about 10 or about 100 kg, more preferably of at least about 250 kg, even more preferably of at least about 500 kg, at least about 1000 kg or even at least about 2500 kg, at least about 3000, at least about 4000 kg, at least about 5000 kg, or more. The amount of plants or parts from the species *Solanum glaucophylluin* may be selected by a skilled person on basis of the specific requirements, e.g. the industrial plant used, the amount to be processed actually, etc. The plants or parts from the species *Solanum glaucophyllum* such as the leaves may be ground, percolated and/or macerated in the above defined alcohol based solvent. Grinding, percolation and/or maceration may be used in the extraction step a).

E.g. percolation may be carried out by any method known in the art, preferably by filling the plants of parts thereof from *Solanum glaucophyllum*, e.g. leaves, into at least one vessel, (wherein, depending on the type of industrial plant, without being limited thereto, at least one, or 2, 3, 4, 5 or even more (cyclically filled) vessels may be used), adding a solvent as defined above to the mixture. The alcohol based solvent may be selected as defined above for extraction step a) in general. Preferably, the solvents for percolation additionally may comprise additives as defined above for extraction step a) in general. Furthermore, pH-value and temperatures used during the extraction process in industrial scale may be selected as defined above in general, wherein such conditions are preferably selected, which lead to an efficacy of extraction of greater than 3 (corresponding to Table 1 below, Example 1A). Preferably, a pH-value of about 4.0 to about 8.0, more preferably a specific pH-value of about 5.5 to about 6.5 may be used. Preferably, the mixture is heated to the above temperatures, preferably between about 40° C. and about 75° C., more preferably between about 40° C. and about 60° C. The process of percolating may be carried out as a continuous process, a semi-continuous process, or any further process, which allows pumping/moving the above alcohol based solvent with a specific flow rate in the at least one vessel. Preferably, such a flow rate is about 500 to 1500 liters per hour, more preferably, about 800 to 1200 liters per hour, and most preferably about 1000 liters per hour. The extraction time may vary as defined above, e.g. from about 6 to about 48 hours and is preferably about 24 hours. The extract obtained by percolation may be filtered, concentrated and/or dried as described above.

According to a particularly preferred embodiment, the extraction according to step a) of the inventive method for preparation and purification of an enriched extract from *Solanum glaucophyllum*, if carried out in industrial scale, is a percolation type extraction and comprises the following specific substeps (Extraction Process EP):

EP1) filling plants or parts thereof from the species *Solanum glaucophyllum* in at least one (cyclically filled) vessel, e.g. in the above defined amounts;

EP2) adding alcohol based solvent, wherein the alcohol based solvent is preferably selected from a mixture of ethanol/water as defined above, e.g. having a ratio (%) of about 25/75, or alternatively of about 75/25 ethanol/water (v/v), wherein the solvent/drug ratio is preferably as defined above, e.g. about 7-12 (v/w), most preferably about 9 (v/w);

EP3) optionally adjusting the pH to about 5.5-6.5 as defined above;

EP4) extracting the plants or parts from the species *Solanum glaucophyllum* in the alcohol based solvent, preferably with a flow rate of 800-1200 liters per hour, more preferably of 1000 liter/hour; preferably for 6-48 hours, more preferably for 24 hours;

EP5) heating the mixture during extraction to a temperature as defined above, preferably about 40-75° C., more preferably about 40-60° C.;

EP6) optionally concentrating the plant extract of step EP4 and EP5 under vacuum as defined above, e.g. by evaporating the organic solvents first and then water until a solution is obtained which contains about 75-65% water and about 25-35% non-volatile matter; and EP7) optionally spray-drying, band drying, or lyophilizing the (concentrated) plant extract.

Alternatively, a maceration may be carried out as defined above, typically using a reactor vessel comprising a mixer or a mixing unit and preferably a heating system. Furthermore, maceration may be carried out by filling the leaves into the vessel, adding the alcohol based solvent as defined above and heating and mixing the mixture (in the vessel), preferably within the above extraction time limits and the above temperatures and pH-values. Preferably, the alcohol based solvent for maceration additionally comprises at least one additive as defined above for extraction step a) in general. The alcohol based solvent may furthermore be selected in a ratio (%) of ethanol/water (v/v) as defined above for extraction step a) in general. Furthermore, pH-value and temperatures used during the extraction process in industrial scale may be selected as defined above in general, wherein such conditions are preferably selected, which lead to an efficacy of extraction of greater than 3 (corresponding to Table 1 below, Example 1A). Preferably, a pH-value of about 4.0 to about 8.0, more preferably a specific pH-value of about 5.5 to about 6.5 may be used. Preferably, the temperature is about 55° C. for 24 hours. The extract obtained by maceration may be filtered, washed, concentrated and/or dried as described above.

According to particularly preferred embodiment, the extraction according to step a) of the inventive method for preparation and purification of an enriched plant extract from *Solanum glaucophyllum*, if carried out in industrial scale, is a maceration type extraction and comprises the following specific substeps (Extraction Process EM):

EM1) filling plants or parts thereof from the species *Solanum glaucophyllum* in at least one vessel, preferably equipped with a mixer and preferably with a heater;

EM2) adding an alcohol based solvent, wherein the alcohol based solvent is preferably selected from a mixture of ethanol/water as defined above, e.g. having a ratio (%) of about 65/35 ethanol/water (v/v), wherein the solvent/drug ratio is preferably as defined above, e.g. about 4-6 (v/w), most preferably about 5 (v/w); the alcohol based solvent preferably additionally containing an additive as defined above, e.g. 0.1% ascorbic acid;

EM3) optionally adjusting the pH to about 5.5-6.5 as defined above, preferably about 5.5;

EM4) extracting the plants or parts thereof from the species *Solanum glaucophyllum* in the alcohol based solvent at a temperature and a time as defined above, preferably about 55° C. for about 24 hours;

EM4) withdrawing the plant extract from the vessel and filtering same, e.g. by pumping it through a 50 pm mesh width;

EM5) optionally washing the remaining solid of the extraction of steps EM4 and EMS one or two times with the same mixture of ethanol/water as defined above, preferably having a solvent/drug ratio of about 3;

EM6) optionally concentrating the plant extract under vacuum by evaporating the organic solvents first and then water until a solution is obtained which contains 75-65% water and 25-35% non-volatile matter; and EM7) optionally spray-drying, band drying, or lyophilizing the (concentrated) plant extract.

The inventive method for preparation and purification of a plant extract from *Solanum glaucophyllum* furthermore comprises purification step b) for purifying the extract obtained according to extraction step a). Such purification step b) is crucial for the inventive method to obtain the main principles of the inventive plant extract in good yields, i.e. both the 1,25-dihydroxyvitamin $D_3$ glycosides and flavonols, particularly quercetin glycosides. The most surprising result was that a good yield in the purification step b) is mainly dependent on application of the extract to a column comprising a non-ionic polymer resin, which was not to be expected from a skilled person based on the prior art. Only use of such a non-ionic polymer resin allows an effective enrichment of the two main principles of the inventive enriched plant extract from *Solanum glaucophyllum* and leads to a significantly higher yield of these active principles, i.e. both the 1,25-dihydroxyvitamin $D_3$ glycosides and flavonols, particularly quercetin glycosides. Such an enrichment of both active principles is not possible with other column materials. Methods known in the art for the isolation of plant components in technical size, as indicated in the introductory part of the description, comprise distillation, solvent-solvent (counter-current) extractions in a first choice followed by chromatographic methods such as column chromatography. Such chromatographic processes typically can be omitted only in few cases, for example when the product of interest possesses special physico-chemical properties which allows to obtain a sufficiently purified product using only liquid-liquid extraction or distillation. However, in the art, all known attempts of purification had the goal of obtaining a pure active vitamin D product but not a combination of the above two active principles. Given the need of chromatography for further purification, experts skilled in the art have always chosen silica material and Sephadex as materials for chromatographic purification of plant extracts as can e found in the literature (see above). Both methods, i.e. silica material and Sephadex, as found by the inventors of the present invention, have significant draw-backs on co-purification of both active principles: the chromatography on silica material gives lower yields of 1,25-dihydroxyvitamin $D_3$ while Sephadex chromatography solely enriches 1,25-dihydroxyvitamin $D_3$ but discriminates the flavonols as demonstrated in lane 9 in FIG. 6. Such materials are thus not suitable for the co-purification of the two active principles having slightly different physico-chemical properties. In this respect, flavonols are a component, which was apparently neither regarded as important for treatment nor has there been any attempt to purify plant extracts comprising both active principles. Accordingly, an expert in the field would always have chosen a method for purifying a plant extract, comprising a Vitamin D metabolite as a main component on the basis of silica material or Sephadex as mentioned above. The inventors of the present invention have also found, that ionic polymer resins (see de Boland et al., supra) are not an adequate alternative, because the salt content of the plant extract was found to overflow the capacity of the column, which requires ionic salts for elution.

In contrast to what was expected by a skilled person from the prior art, the present inventors surprisingly found, that non-ionic polymer resins are generally suited for the object given, namely a method which provides a combination of the two active principles, i.e. both the 1,25-dihydroxyvitamin $D_3$ glycosides and flavonols, particularly quercetin glycosides, and in which the content of these active principles is close to an optimum and the alkaloid content is close to a minimum.

Accordingly, purification step b) for purifying the extract obtained according to step a) preferably comprises the following steps:

b1) applying the plant extract obtained according to step a) to a column comprising a non-ionic polymer resin;
b2) optionally washing the column with water and/or an alcohol based solvent as defined above;
b3) eluting the enriched plant extract from the column; and
b4) optionally drying the enriched plant extract.

According to substep b1) of purification step b) of the inventive method for preparation and purification of an enriched plant extract from *Solanum glaucophyllum*, the extract is applied to a column comprising a non-ionic polymer resin. In the context of the present invention, non-ionic polymer resins suitable for substep b1) of step b) may comprise (porous or non-porous) non-ionic polymer resins, including, without being limited thereto, polystyrene, styrene-divinylbenzene copolymers, acrylic ester polymers, and polyphenolic resins. More preferably, the (porous or non-porous) non-ionic materials are selected from Amberlite XAD-1, XAD-2, XAD-4, XAD-5 (which are trademarks, and manufactured by Rohm and Haas Co., U.S.A. wherein these resins are composed of styrene-divinylbenzene copolymer) and Diaion HP1 0, HP20, HP30, HP40, HP50 (which are trademarks, and manufactured by Mitsubishi Chemical Co., Japan, wherein these resins are composed of styrene-divinylbenzene copolymer), Amberlite XAD-7, XAD-7 HP, XAD-8 or XAD-1 180 (trademarks for adsorbents composed of acrylic ester polymer, manufactured by Rohm and Haas Co.), and Duolite S-30 (trademark for an adsorbent composed of phenolic resin, manufactured by Chemical Process Co., U.S.A.), or non-ionic polymer resins being equivalent to the above specifically mentioned resins, e.g. any equivalent resin from any other supplier, even more preferably, (porous or non-porous) non-ionic materials suitable for step b) of the inventive method are selected from resins Amberlite XAD-resins including Amberlite XAD-1, XAD-2, XAD-4, XAD-5, and Amberlite XAD-7, XAD-7 HP, XAD-8 or XAD-1 180, and most preferably from resins Amberlite XAD-7, XAD-7 HP, XAD-8 or XAD-1180, or such non-ionic polymer resins being equivalent to the above specifically mentioned resins, e.g. any equivalent resin from any other supplier.

Furthermore, the non-ionic materials suitable for substep b1) of purification step b) preferably shall not comprise Dextran-based resins, more preferably no Sephadex or Superdex resin material, and even more preferably no non-ionic Sephadex or Superdex resin material, which are preferably explicitly disclaimed from the subject matter of the present invention from non-ionic materials suitable for step b).

Applying the plant extract to a column in substep b1) of purification step b) of the inventive method for preparation and purification of an enriched plant extract from *Solarium glaucophyllum* may be carried out using any method suitable in the art. Without being limited thereto, such methods may comprise the use of syringes, etc., if the inventive method is carried out at laboratory scale, or of pumps, etc., if the inventive method is carried out at industrial scale, etc. Preferably, columns are used for applying the plant extract, having a length/width ration of about 2 to 6. The columns may be pre-washed prior to use with a solvent as defined herein, preferably with an alcohol based solvent as defined above, and/or with water and/or with acetone. The column may be furthermore be equilibrated prior to use, preferably using water or an alcohol based solvent as defined above, wherein the column preferably does not run dry during equilibration. When applying the plant extract to the column according to substep b1) of purification step b), the plant extract (as an aqueous solution due to the content of a solvent as defined above) may be applied or pumped to the top of the column, preferably with a speed of 1, 2, 3, 4, 5 or more bed volumes, preferably 3 bed volumes. The same plant extract obtained according to extraction step a) may be applied several times to the column, e.g. once, twice, 3-times, 4-times, 5-times or even more, wherein the first (typically clear) eluent of the column may be discarded.

According to optional substep b2) of purification step b) of the inventive method for preparation and purification of an enriched plant extract from *Solanum glaucophyllum* the column with the applied plant extract, is optionally washed with water and/or an alcohol based solvent as defined above. If an alcohol based solvent is used, such alcohol based solvent may be any alcohol based solvent as mentioned above, preferably such an alcohol based solvent, which typically does not contain an amount of alcohol higher than 20% (v/v) in order to minimize or prevent an early elution of the enriched plant extract or any of its components from the column. Particularly suitable alcohol based solvents may be selected, without being limited thereto, from an ethanol/water mixture having a ratio (%) of about 0/100 to about 20/80 ethanol/water (v/v), e.g. may be selected from an ethanol/water mixture having a ratio (%) of about 0/100 ethanol/water (v/v), about 5/95 ethanol/water (v/v), about 10/90 ethanol/water (v/v), about 15/85 ethanol/water (v/v), or about 20/80 ethanol/water (v/v), more preferably an ethanol/water mixture having a ratio (%) of about 5/95 ethanol/water (v/v), about 10/90 ethanol/water (v/v), or about 15/85 ethanol/water (v/v). Alternatively, but less preferred, the alcohol based solvent of substep b2) of purification step b) of the inventive method may be selected from a methanol/water mixture having a content of methanol/water as described above for the ethanol/water mixture. The optional washing step according to substep b2) of purification step b) of the inventive method for preparation and purification of an enriched plant extract from *Solanum glaucophyllum* may be carried out at least once, preferably 1-2 times, optionally 1-3 times, 1-4 times, 1-5 times or more. The washing according to substep b2) of step b) of the inventive method may follow a specific sequence of water and/or alcohol based solvents. E.g. the column may be washed in a first step at least once with water or any of the above mentioned alcohol based solvents, preferably water, e.g. once, twice, 3 times, etc., e.g. once with water. A first washing with water or another solvent is preferably carried out until the eluent becomes colorless. Then, in a second optional washing step, a further washing procedure may follow, using a different solvent, i.e. water or alcohol based solvents as defined above, preferably an alcohol based solvent having a concentration as specifically mentioned above. The column preferably may be washed in a second step at least once, twice, 1-3 times, 1-4 times, 1-5-times or even more, preferably 1-3 times with an alcohol based solvent as defined above. The alcohol based solvent is preferably as defined above. Such a second optional washing is preferably carried out using 1, 2, 3, 4, 5, (1-2, 13, 1-4, 1-5), or more bed volumes (of the column), preferably 1 to 3 bed volumes (of the column).

According to substep b3) of purification step b) of the inventive method for preparation and purification of an enriched plant extract from *Solanum glaucophyllum* the enriched plant extract is eluted from the column. For elution from the column a solvent as described above may be selected, including an alcohol, such as ethanol, methanol, isopropanol, preferably ethanol or methanol, or a keton, such as aceton, or a suitable alcohol based solvent as defined above. A suitable alcohol based solvent may comprise any alcohol based solvent as defined above, e.g. an ethanol/water mixture, without being limited thereto, having a ratio (%) of about 100/00 to about 70/30 ethanol/water (v/v), e.g. having a ratio (%) of about 100/00 ethanol/water (v/v), about 95/5 ethanol/water (v/v), about 90/10 ethanol/water (v/v), about 85/15 ethanol/water (v/v), about 80/20 ethanol/water (v/v), about 75/25 ethanol/water (v/v), or about 70/30 ethanol/water (v/v). More preferably, the ethanol/water mixture may be selected from an ethanol/water mixture having a ratio (%) of about 100/00 ethanol/water (v/v) to about 95/5 ethanol/water (v/v), most preferably of about 95/5, 96/4, 97/3, 98/2, 99/1 or 100/0 ethanol/water (v/v). Alternatively, but less preferred, the alcohol based solvent of substep b3) of purification step b) of the inventive method may be selected from a methanol/water mixture having a content of methanol/water as described above for the ethanol/water mixture or from an isopropanol/water mixture having a content of isopropanol/water as described above for the ethanol/water mixture. For elution of the enriched plant extract from the column according to substep b3) of purification step b) the solvent is applied to the column using 1, 2, 3, 4, 5, (1-2, 1-3, 1-4, 1-5), or more bed volumes (of the column), preferably 2 to 5 bed volumes (of the column).

According to an optional substep b4) of purification step b) of the inventive method for preparation and purification of an enriched plant extract from *Solanum glaucophyllum* the enriched plant extract optionally may be dried as already described above for extraction step a). Preferably, the plant extract may be dried without being limited thereto, e.g., by spray-drying, band drying, lyophilizing, etc., preferably to a content of about or near to 100% non-volatile matter, e.g. a content of about 10-0% water and about 90-100% non-volatile matter, each value determined on basis of the total weight the plant extract prior to drying, e.g. as obtained according to substep b3) of purification step b) subsequent to elution.

Drying the plant extract according to optional substep b4) of purification step b) of the inventive method for preparation and purification as defined above, may furthermore be combined with or followed by a heat-/high temperature treatment as defined above for extraction step a) in order to increase the shelf life of the enriched plant extract, preferably to allow storage of the enriched plant extract, e.g. if the extract is to be stored prior to use.

According to one particularly preferred embodiment, the purification according to step b) of the inventive method for preparation and purification of an enriched extract from *Solanum glaucophyllum*, preferably if carried out in laboratory scale, comprises the following specific features (Purification Process PL)

PL1) applying the plant extract obtained according to step a) to a column comprising a non-ionic polymer resin, preferably selected from Amberlite XAD-7 HP or XAD-1 180 or any equivalent resin from any other supplier;

PL2) washing the column once, preferably at least twice, optionally 3 times, with water, preferably until the effluent is colorless; and washing the column at least once with an ethanol/water mixture preferably having a ratio (%) as defined above, e.g. between about 0/100 ethanol/water (v/v) and about 10/90 ethanol/water (v/v), more preferably about 5/95 ethanol/water (v/v), preferably with 1-3 bed volumes; and PL3) elution of the enriched plant extract from the column using an alcohol based solvent as defined above, preferably an ethanol/water mixture, more preferably having a ratio (%) as defined above, e.g between about 95/5 ethanol/water (v/v) and about 100/0 ethanol/water (v/v), most preferably about 96/4 ethanol/water (v/v), preferably with 2-5 bed volumes.

PL4) optionally drying the enriched plant extract obtained according to step PL3).

According to one particularly preferred embodiment, the purification according to step b) of the inventive method for preparation and purification of an enriched extract from *Solanum glaucophyllum*, preferably if carried out in industrial scale, comprises the following specific features (Purification Process PF):

PF1) applying the plant extract obtained according to step a), preferably using a percolation (type extraction) process (process steps EP1 to EP7), more preferably with an ethanol/water mixture having a ratio (%) of about 25/75 ethanol/water (v/v), to a column comprising a. non-ionic polymer resin, preferably selected from Amberlite XAD-7 HP or XAD-1 180 or any equivalent resin from any other supplier; and reapplication of the column effluent back to the column, preferably three times;

PF2) washing the column at least once with water, preferably until the effluent is colorless; and washing the column at least once with an ethanol/water mixture having a ratio (%) of about 10/90 ethanol/water (v/v) to about 0/100 ethanol/water (v/v), preferably with 2 bed volumes; and PF3) elution of the enriched plant extract from the column using an ethanol/water mixture having a ratio (%) of about 95/5 ethanol/water (v/v) to about 100/0 ethanol/water (v/v), preferably of about 96/4, 97/3, 98/2, 99/1 or about 100/0 ethanol/water (v/v), most preferably of about 96/4 ethanol/water (v/v).

PF4) optionally drying the enriched plant extract obtained according to step PF3).

According to a further particularly preferred embodiment, the purification according to step b) of the inventive method for preparation and purification of an enriched extract from *Solanum glaucophyllum*, preferably if carried out in industrial scale, comprises the following specific features (Purification Process ES):

PS1) applying the plant extract obtained according to step a), preferably using a maceration (type extraction) process (process steps EM1 to EM7), more preferably with an ethanol/water mixture having a ratio (%) of about 65/35 ethanol/water (v/v), to a column comprising a non-ionic polymer resin, preferably selected from Amberlite XAD-7 HP or XAD-1 180 or any equivalent resin from any other supplier; and reapplication of the column effluent back to the column, preferably three times;

PS2) washing the column at least once with water, preferably until the effluent is colorless; and washing the column at least once with an ethanol/water mixture having a ratio (%) of about 10/90 ethanol/water (v/v) to about 0/100 ethanol/water (v/v), preferably with 2 bed volumes; and PS3) elution of the enriched plant extract from the column using an ethanol/water mixture having a ratio (%) of about 95/5 ethanol/water (v/v) to about 100/0 ethanol/water (v/v), preferably of about 96/4, 97/3, 98/2, 99/1 or 100/0 ethanol/water (v/v), most preferably 96/4 ethanol/water (v/v)

Any of the above mentioned alternatives mentioned above may be combined with each other. Particularly industrial extraction processes EP or EM (or the laboratory extraction process) may be combined with industrial purification processes PF or PS, as suitable.

Enriched Plant Extracts

The present invention is furthermore directed to an enriched plant extract from *Solanum glaucophyllum* as a direct product of the inventive method for preparation and purification of an enriched plant extract from *Solanum glaucophyllum* as defined above, i.e. obtained or obtainable by the inventive method as defined above. Such an enriched plant extract is specifically characterized by its specific and advantageous composition, which can only be obtained using the specific features according to the above inventive method. More particularly, such an inventive enriched plant extract, directly obtained or obtainable using the above inventive method, preferably shows the following composition:

As active ingredients:

Vitamin $D_3$ metabolites in a concentration of preferably at least 300 µg/g, preferably of more than 500 µg/g, even more preferably of more than 2000 µg/g of active Vitamin $D_3$, preferably analytically determined as total 1,25-dihydroxyvitamin $D_3$, preferably present as a glycoside or a mixture of different glycosides of 1,25-dihydroxyvitamin $D_3$, or more preferably a 1,25-dihydroxyvitamin $D_3$-1β-glucopyranoside of the following formula (I):

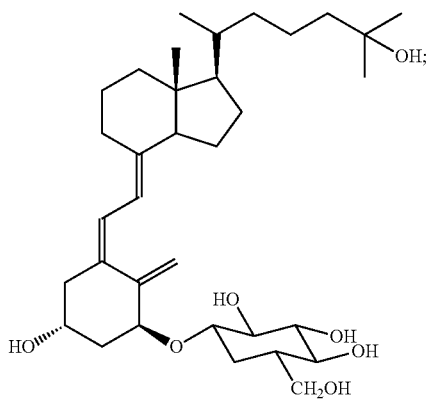

and

Active quercetin glycosides of at least 100 mg/g, more preferably of at least 150 mg/g, and most preferably of at least 200 mg/g, determined as quercetin after acid hydrolysis.

Inactive Components

Optionally, the inventive enriched plant extract obtained by the inventive method may be further characterized by the following contents:

Inorganic matter: maximum preferably 6% (comprising elements Ca, K, Mg and S in the range of 0.1 to 1%, and elements Br, Cl, P, Si, Al, Na, Cu, Fe, Zn in the range of less than 0.1%);

Carbohydrates: preferably between 50-75%;

Proteins: preferably less than 2% (which significantly lowers the potential occurrence of allergies);

Fat preferably less than 2%;

Toxic components

The inventive enriched plant extract obtained by the inventive method may be additionally characterized by a low level of alkaloids. This is particularly noteworthy and advantageous, because plants from the genus *Solanum* are known to contain toxic alkaloids, particularly solasodine in *Solanum glaucophyllum*. Accordingly, the inventive enriched plant extract obtained by the inventive method may be additionally characterized by alkaloids below a detection limit of 10 µg/g (particularly solasodine);

Such an inventive enriched plant extract obtained by the inventive method for preparation and purification of an enriched plant extract from *Solanum glaucophyllum* as defined above provides, interalia, following superior chemical properties over extracts of the art:

Occurrence of an enriched content of both the active principles, which represent two classes of bone-active components: 1,25-dihydroxyvitamin D3 and the flavonol quercetin, both in glycosidic bound form;

An intrinsic water solubility, which allows a simple, not complicated formulation, wherein no addition of detergent is necessary;

Low browning/discolorization (as has been found that browning/discolorization reactions are undesirable because this lowers the content of plant phenols such as flavonols).

The enriched plant extract obtained by the inventive method also provides, inter alia, following superior biological properties over extracts of the art:

A high Vitamin D activity, solely due to the most active principle 1,25-dihydroxyvitamin $D_3$;

A superior biological tolerance of the 1,25-dihydroxyvitamin $D_3$-1β-glucopyranoside of the above formula (I) over the parent compound 1,25-dihydroxyvitamin $D_3$ due to its glycoside structure (which acts as a prodrug form of the endogenous active vitamin D metabolite 1,25-dihydroxyvitamin $D_3$);

A faster entry of the therapeutic effect compared to Vitamin $D_3$ alone;

A significant opening of the therapeutic window due to the presence of an enriched content of both the two bone active principles, the 1,25-dihydroxyvitamin $D_3$ glycosides and flavonoids, particularly quercetin glycosides in the inventive plant extract, which lowers the risk of hypercalcemia;

The inventive plant extract shows superior properties in relieving lameness and improving bone strength in meat producing animals;

The inventive plant extract is highly active in improving eggshell quality;

The inventive plant extract is also highly active in preventing a decline of blood calcium during calving (milk fever);

Furthermore, the inventive plant extract is highly active in a FDA-accepted preclinical rat model for human osteoporosis. In an experiment, in which an unpurified extract of *Solanum glaucophyllum* was applied to ovariectomized female rats (an animal model which stimulates human female post-menopausal osteoporosis)

showed anti-osteoporotic effects but also calcium deposits in soft tissues, whereas the purified extract of the same Vitamin D content and obtained by the inventive method as described above, showed an anti-osteoporotic effect but no soft tissue calcification.

Based on the above surprising results, one embodiment of the present invention is also directed to a (synthetic) plant extract composition, preferably comprising following components:

a) A Vitamin D active component, preferably a 1-alpha-hydroxy substituted Vitamin D metabolite or more preferably 1,25-dihydroxyvitamin $D_3$, in free and/or in glycosidic bound form from a natural or a synthetic source, preferably analytically determined as total 1,25-dihydroxyvitamin $D_3$, more preferably present a glycoside or a mixture of different glycosides of 1,25-dihydroxyvitamin Dar or more preferably a 1,25-dihydroxyvitamin $D_3$-1β-glucopyranoside of the following formula (I):

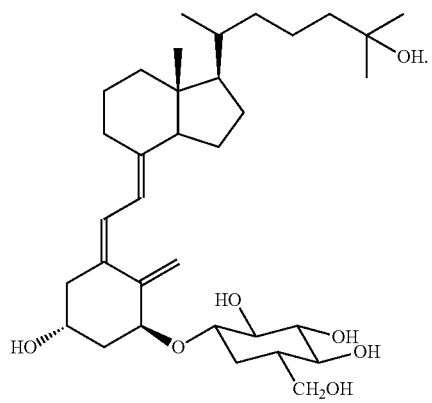 [SMILES: C=C1/C(=C\C=C2/CCC[C@@]3(C)C2CC[C@@H]3C(C)CCCC(C)(C)O)C[C@@H](O)C[C@@H]1OC1CC(CO)C(O)C(O)C1O]

preferably in a concentration of at least 300 μg/g, preferably of more than 500 μg/g, even more preferably of more than 2000 μg/g, of active Vitamin $D_3$; and b) at least one (active) flavonol in a concentration of at least 100 mg/g, more preferably of at least 150 mg/g, and most preferably of at least 200 mg/g.

In the context of the present invention flavonols, as contained in the inventive (synthetic) plant extract composition, may be selected from any flavonols or their glycosides known in the art, preferably from flavonols or their glycosides known to have a beneficial therapeutic effect on bone growth. Such flavonols may be selected from compounds including myricetin, quercetin, kaempferol, fisetin, isohamnetin, pachypodol, rhamnazin, patuletin, eupalitin, eupatolitin, 5-hydroxyflavone, 6-hydroxyflavone, 7-hydroxyflavone, 5-hydroxy-7-methoxyflavone, 7-hydroxy-5-methylflavone, or their glycosides, etc. More preferably, the flavonols, as contained in the inventive (synthetic) plant composition, may be selected from glycosides of the above flavonols, e.g. from glycosides from myricetin, quercetin, kaempferol, fisetin, isohamnetin, pachypodol, rhamnazin, patuletin, eupalitin, eupatolitin, 5-hydroxyflavone, 6-hydroxyflavone, 7-hydroxyflavone, 5-hydroxy-7-methoxyflavone, 7-hydroxy-5-methylflavone, etc., particularly preferably from quercetin and its glycosides.

Pharmaceutical Compositions

According to another specific embodiment, the present invention is also directed to a pharmaceutical composition comprising:

(a) an inventive enriched plant extract as defined above or a (synthetic) plant composition as defined above, (or the components of the plant extract, particularly 1,25-dihydroxyvitamin $D_3$ glycosides and flavonols, more particularly quercetin glycosides, as defined above); and (b) optionally a pharmaceutically acceptable carrier and/or vehicle.

The inventive pharmaceutical composition may comprise (a) an inventive (synthetic) plant composition, or its components, as defined above, preferably in the above concentrations.

The inventive pharmaceutical composition may furthermore comprise (b) a pharmaceutically acceptable carrier and/or vehicle. In the context of the present invention, a pharmaceutically acceptable carrier or vehicle of the inventive pharmaceutical composition typically refers to a non-toxic carrier or vehicle that does not destroy the pharmacological activity of the components of the plant extract, particularly of 1,25-dihydroxyvitamin $D_3$ glycosides and flavonols, more particularly quercetin glycosides, with which it is formulated.

Pharmaceutically suitable carriers or vehicles, that may be used in the inventive pharmaceutical composition, may be typically distinguished into solid or liquid carriers or vehicles, wherein a specific determination may depend on the viscosity of the respective carrier or vehicle to be used.

In this context, solid carriers and vehicles typically included e.g., but are not limited to, ion exchangers, alumina, aluminum stearate, lecithin, and salts, if provided in solid form, such as protamine sulfate, disodium hydrogen phosphate, potassium hydrogen phosphate, sodium chloride, zinc salts, colloidal silica, magnesium trisilicate, or polyvinyl pyrrolidone, waxes, polyethylene-polyoxypropylene-block polymers, wool fat, sugars, such as, for example, lactose, glucose and sucrose; excipients such as maltodextrin, xylitol, starch, including, for example, corn starch or potato starch; or cellulose-based substances, e.g. cellulose and its derivatives, such as, for example, sodium carboxymethylcellulose, ethylcellulose, cellulose acetate; pulverized tragacanth; malt; gelatine; tallow; (solid) lubricants, such as, for example, stearic acid, magnesium stearate; calcium sulfate; wetting agents, such as, for example, sodium lauryl sulfate; colouring agents; flavouring agents; drug (active agent) carriers; tablet-forming agents; stabilizers; antioxidants; preservatives; coatings, etc.

Liquid carriers or vehicles, e.g. for aqueous or oleaginous suspensions, typically include, but are not limited to, e.g., water; pyrogen-free water; solutions of ion exchangers, alumina, aluminum stearate, lecithin, or serum proteins, such as human serum albumin; alginic acid; isotonic saline solutions or phosphate-buffered solutions, Ringer's solution, isotonic sodium chloride solution, etc. or salts or electrolytes, if provided in solubilized form, such as protamine sulfate, phosphates, e.g. disodium hydrogen phosphate, potassium hydrogen phosphate, sodium chloride, zinc salts, or (other) buffer substances including e.g. glycine, sorbic acid, potassium sorbate; liquid solutions of polyols, such as, for example, polyethylene glycol, polypropylene glycol, glycerol, 1,3-butanediol, sorbitol, Mannitol; sterile, fixed oils, any suitable bland fixed oil, e.g. including synthetic mono- or di-glycerides, partial glyceride mixtures of saturated vegetable fatty acids, fatty acids, such as oleic acid and its glyceride derivatives, natural pharmaceutically-acceptable oils, e.g. plant oils, such as, for example, groundnut oil, cottonseed oil, sesame oil, corn oil and oil from Theobroma; olive oil or castor oil, especially in their polyoxyethylated versions. These liquid carriers or vehicles may also contain or comprise a long-chain alcohol diluent or dispersant, such as carboxymethyl cellulose or similar dispersing agents, or commonly used surfactants or emulsifiers, such as Tween®, Spans and other emulsifying agents or bioavailability enhancers, etc., if provided in a liquid form.

The inventive pharmaceutical composition may be administered orally, rectally, via an implanted reservoir or optionally parenterally.

Preferably, the inventive pharmaceutical composition as defined above may be administered orally (or rectally) in any orally (or rectally) acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. If desired, certain sweetening, flavoring or coloring agents may also be added. For oral administration in a capsule form, useful diluents include lactose and dried cornstarch. For the preparation of capsules particularly carriers and vehicles may be used, preferably selected from excipients such as maltodextrin, xylitol, starch, including, for example, corn starch or potato starch; etc.; For the preparation of tablets particularly carriers and vehicles may be used, preferably selected from lubricants, including for example, stearic acid, magnesium stearate; excipients such as maltodextrin, xylitol, starch, including, for example, corn starch or potato starch; and coatings suitable for tablets, etc. Retard forms of those tablets and capsules are also envisaged, i.e. a form of retarded release, wherein the retard form preferably comprises the active principles as mentioned above embedded in a biodegradable biopolymer or wherein the active principles as mentioned above are enwrapped with a cover (for slow release), which allows controlled diffusion of the active principles. When aqueous suspensions are required for oral use, the active ingredient may be e.g. combined with emulsifying and suspending agents. Such formulations may also be used for rectal administration or for administration via an implanted reservoir.

The inventive pharmaceutical composition typically comprises a "safe and effective amount" of the at least one of the both main principles, the 1,25-dihydroxyvitamin $D_3$ glycosides and flavonols, more particularly quercetin glycosides, as defined herein. As used herein, a "safe and effective amount" means an amount of these main principles, that is sufficient to significantly induce a positive modification of a disease or disorder as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of both main principles, the 1,25-dihydroxyvitamin $D_3$ glycosides and flavonols, more particularly quercetin glycosides, as defined herein, will furthermore vary in connection with the particular condition to be treated and also with the age and physical condition of the patient to be treated, the body weight, general health, sex, diet, time of administration, rate of excretion, drug combination, the activity of the employed specific autoantigenic protein and/or antibody as defined herein, the severity of the condition, the duration of the treatment, the nature of the accompanying therapy, the particular pharmaceutically acceptable carrier used, and similar factors, within the knowledge and experience of the accompanying doctor. The inventive pharmaceutical composition may be used for human and also for veterinary medical purposes.

Applications of the Inventive Plant Extract from *Solanum glaucophyllum* and the Inventive Pharmaceutical Composition The inventive pharmaceutical composition, the inventive enriched plant extract, obtained or obtainable by the inventive method for preparation and purification of an enriched plant extract from *Solanum glaucophyllum* as defined above, the inventive (synthetic) plant extract composition, or both the main components of the inventive enriched plant extract or the inventive (synthetic) plant extract composition, i.e. both 1,25-dihydroxyvitamin $D_3$ glycosides and flavonols, particularly quercetin glycosides, as defined above, may be administered to a human or animal in need thereof to treat any of the diseases as defined herein, particularly:

bone mass reduction-related diseases, e.g. Osteopenia or (senile or post-menopausal) Osteoporosis, particularly in human beings;

Tibial Dyschondroplasia and other bone related mineralization-related leg problems, preferably in poultry, more preferably in chickens, turkeys, geese and ducks;

hypocalcemic paresis around parturition, also known as parturient paresis in milk producing animals or milk fever, particularly in cattle and other milk producing animals. This also involves any diseases related to a decline of plasma calcium during calving in cattle and other milk producing animals. In this context, milk fever is a metabolic disease in milk-producing animals around parturition, when reconstituting milk production depletes circulating calcium in mother blood. The endogenous calcium homeostasis is not able to wobiiize enough calcium from feed or bone to prevent a fall in blood calcium. In certain cases the low calcium concentration induces muscle paresis. Today's treatment consists of applying large calcium doses around calving (see: The Merck Veterinary Manual, Parturient Paresis in Cows), which is inferior to application of the inventive plant extracts.

Administration for any of the diseases as defined herein may occur as described above for the inventive pharmaceutical composition, particularly the modes of administration and the safe and effective amount to be administered.

Accordingly, a further embodiment of the present invention is also directed to the use of the inventive enriched plant extract, obtained or obtainable by the inventive method for preparation and purification of an enriched plant extract from *Solanum glaucophyllum* as defined above, the use of the inventive (synthetic) plant extract composition, or use of both the main components of the inventive enriched plant extract or the inventive (synthetic) plant extract composition as defined above, i.e. both 1,25-dihydroxyvitamin $D_3$ glycosides and flavonols, particularly quercetin glycosides, as defined above, for the preparation of a(n inventive) pharmaceutical composition for the prevention or treatment of a disease or a condition as defined herein, particularly prevention and treatment of bone mass reduction-related diseases, e.g. Osteopenia or (senile or post-menopausal) Osteoporosis, particularly in human beings, particularly prevention and treatment of Osteopenia during adulthood in humans, or prevention and treatment of Osteopenia in companion animals; prevention and treatment of Tibial Dyschondroplasia and other bone related mineralization-related leg problems including improvement of bone mass and breaking strength, preferably in poultry, more preferably in chickens, turkeys, geese and ducks; improvement of eggshell strength and thickness in poultry; enhancement of calcium and phosphate uptake in poultry and pigs and thus reduction or prevention of (increased) discharge of phosphor into urine and manure; hypocalcemic paresis around parturition, also known as parturient paresis in milk producing animals or milk fever, particularly in cattle and other milk producing animals. This also involves any diseases related to a decline of plasma calcium during calving in cattle and other milk producing animals, etc.

Another embodiment of the present invention is directed to the inventive enriched plant extract, obtained or obtainable by the inventive method for preparation and purification of an enriched plant extract from *Solanum glaucophyllum* as defined above, the use of the inventive (synthetic) plant extract composition, or the use of both the main principles of the inventive enriched plant extract or the inventive (synthetic) plant extract composition, i.e. both 1,25-dihydroxyvitamin $D_3$ glycosides and flavonols, particularly quercetin glycosides, as defined above, as a dietary supplement for human or veterinary use. Such dietary supplement may be administered without occurrence or detection of a disease state of any of the diseases as mentioned above, particularly bone mass reduction-related diseases, such as Osteopenia or Osteoporosis, Tibial Dyschondroplasia, parturient paresis in milk producing animals or milk fever, etc., i.e. for non-therapeutical reasons or as a prophylaxis for the above diseases.

Finally, the present invention also relates to a kit, particularly a kit of parts, comprising the inventive enriched plant extract, obtained or obtainable by the inventive method for preparation and purification of an enriched plant extract from *Solanum glaucophyllum* as defined above, the inventive (synthetic) plant extract composition, both the main components of the inventive enriched plant extract, i.e. both 1,25-dihydroxyvitamin $D_3$ glycosides and flavonols, particularly quercetin glycosides, as defined above, and/or the inventive pharmaceutical composition, and optionally technical instructions or an instruction manual, preferably for any of the above mentioned uses, treatments or therapies.

Advantages of the Present Invention

The present invention advantageously provides a method for preparation and purification of an enriched plant extract from *Solanum glaucophyllum* as defined above, which allows the enriched provision of two separate active principles, 1,25-dihydroxyvitamin $D_3$ glycosides (including 1,25-dihydroxyvitamin $D_3$-1β-glucopyranosides) and flavonols, particularly quercetin glycosides. The inventive enriched plant extract from *Solanum glaucophyllum* as defined above is surprisingly active, as proven in a scientifically accepted preclinical model for human post-menopausal osteoporosis. It is also able to support the essential active Vitamin D metabolite concentration and therefore suitable for subjects with impaired kidney function. The inventive enriched plant extract is also surprisingly active in enhancing calcium and phosphorus uptake in animals, improving bone mass and breaking strength, preventing tibial dyschondroplasia in poultry and preventing a decline of plasma calcium concentration during calving in cattle, known as parturient paresis in milk producing animals. In particular, the inventive enriched plant composition is advantageous due to an enriched content of the two active principles 1,25-dihydroxyvitamin $D_3$ glycosides (including 1,25-dihydroxyvitamin $D_3$-1β-glucopyranos ides) and flavonols, particularly quercetin glycosides, which surprisingly enlarge the formerly extremely small therapeutic window known for 1,25-dihydroxyvitamin $D_3$. This gives the inventive enriched plant extract a surprisingly better tolerance than the free Vitamin $D_3$ metabolite alone. It furthermore reduces the risk of hypercalcemia in comparison to the compound 1,25-dihydroxyvitamin $D_3$ (shown in animal models) used alone in smaller concentrations in clinical use and thus may be safer in humans than shown for the parent compound alone. It has also be found that the onset of the biological response of both active principles of the present composition is faster compared to vitamin D alone, which may be due to the presence of 1,25-dihydroxyvitamin $D_3$ and 1,25-dihydroxyvitamin $D_3$-1β-glucopyranosides in the inventive enriched plant extract, as has been found. Finally, no detectable toxic components linked to the plant raw material are contained in the inventive enriched plant composition. The inventive enriched plant extract from *Solanum glaucophyllum* as defined above also has a low degree of discolorization, and a low allergy potential due to a low content of proteins.

BRIEF DESCRIPTION OF THE FIGURES

The following Figures are intended to illustrate the invention further. They are not intended to limit the subject matter of the invention thereto.

$$yf = VDM_{(extract)} \cdot [Qu_{(extract)}/1000] \cdot ef.$$

As a result of laboratory experiments, the factor of goodness obtained two optima, which were also applicable in industrial scale processes.

Figure 5:
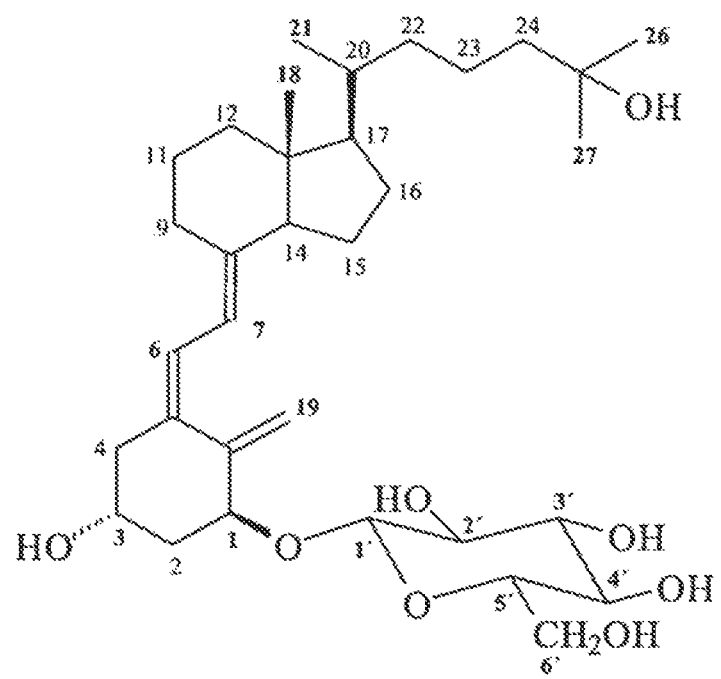

FIG. 5 shows the structure of the component 1,25-dihydroxyvitamin D3 as revealed by UV-, $^1$H-NMR and $^{13}$C-NMR spectra.

Figure 6:
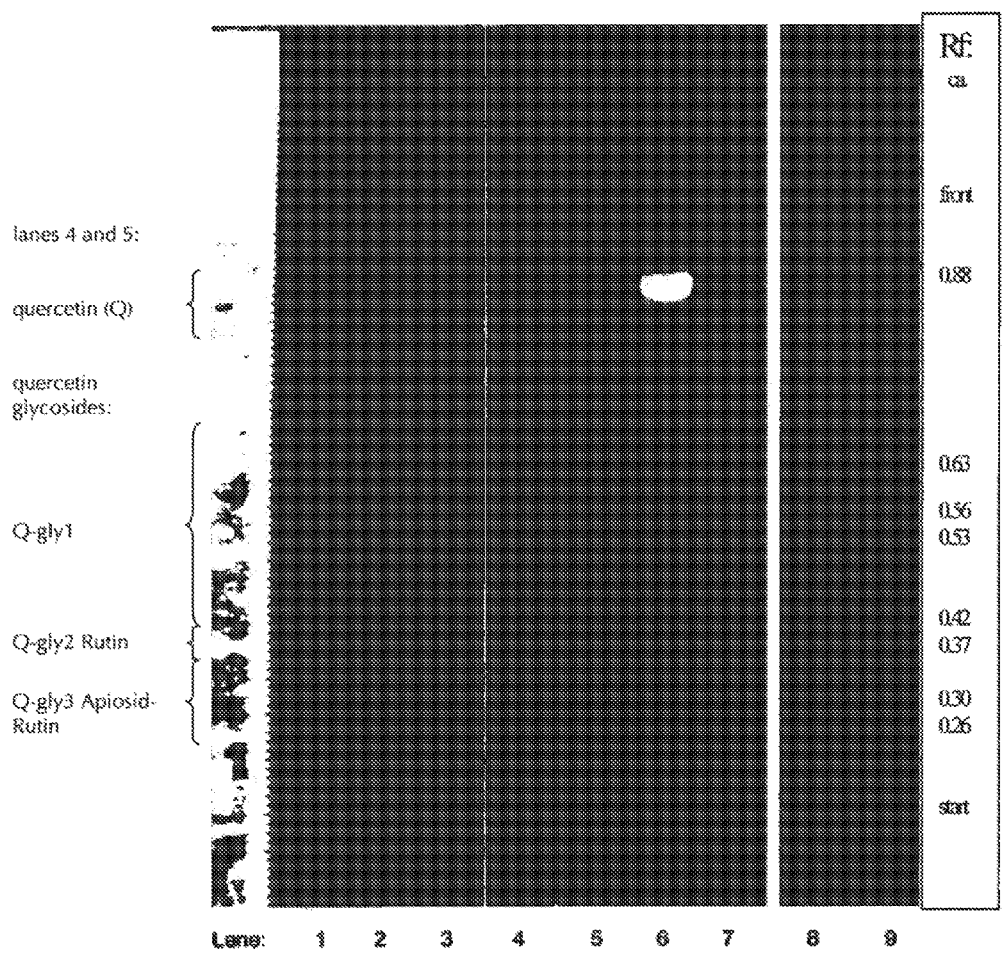

FIG. 6 shows a high performance thin layer chromatographic characterization of the obtained preparation and comparison with standards and with a gingko and a hawthorn extract (see Example 3 (iii)). The conditions were as follows:
  Plates: silicagel G with UV-Indicator 10×10 cm Merck (Camag AG, Muttenz Switzerland)
  Solvent: ethyl acetate/formic acid/acetic acid/water (100+11+11+26). 45 minutes pre-condition, running time 45 minutes
  Detection Naturstoff-Reagent (Camag AG, Muttenz Switzerland)

Application:
  Lane 1: quercetin (rf 0.88; 0.56 µg); hyperosid (rf 0.55; 1.25 µg); chlorogenic acid (rf 0.42, 1.2 µg); rutin (rf 0.37; 0.73 µg)
  Lane 2 kaempferol (rf 0.90; 0.25 µg); isoquercitrin (rf 0.57; 1.25 µg); hyperosid (rf 0.54; 1.25 µg);
  Lane 3 caffeic acid (rf 0.82; 0.1 µg); isoquercitrin (rf 0.57; 1.25 µg)
  Lane 4 purified extract (Batch 1; 41 µg; quercetin and quercetin glycosides are indicated)
  Lane 5 purified extract (Batch 2; 41 µg; quercetin and quercetin glycosides are indicated)
  Lane 6 ginkgo biloba extract (commercial product; 10 µl)
  Lane 7 hawthorn extract (commercial product; 201 µg)
  Lane 8 Standards identical to lane 1
  Lane 9 purified comparative extract according to the art (comparative sample of an extract purified on a Sephadex G10 column. Despite of the high enrichment rate of the vitamin D activity (2000 µg/g) virtually no flavonols are present)

Figure 7:
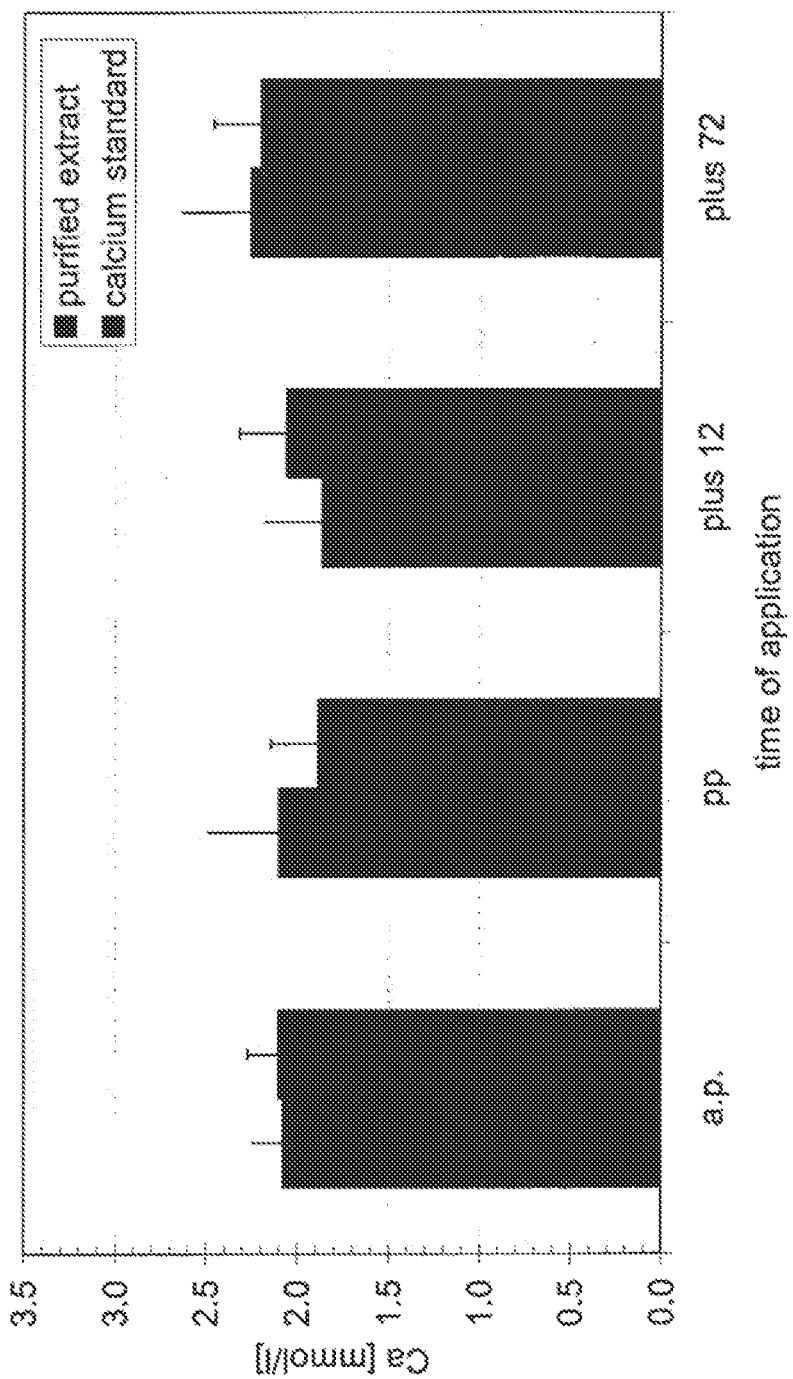

FIG. 7 shows the progression of plasma calcium during calving (parturient paresis). The first column shows the inventive purified plant extract (purified extract), the second column shows treatment with a calcium salt as a bolus application ((Bovicalc, Boehringer Ingelheim, Germany, applied according to the manufacturers instructions). As can be seen, both treatments can prevent a fall in plasma calcium equally (with slightly better levels of calcium with the inventive purified plant extract (purified extract) than with the calcium standard). A clear fall in plasma calcium is inevitable without treatment as can be seen in FIG. 7.

The columns represent: a.p: 24 hours ante partum,
  pp: at parturition (calving);
  plus-12: 12 hours after calving;
  plus-72: 72 hours after calving.

Figure 8:
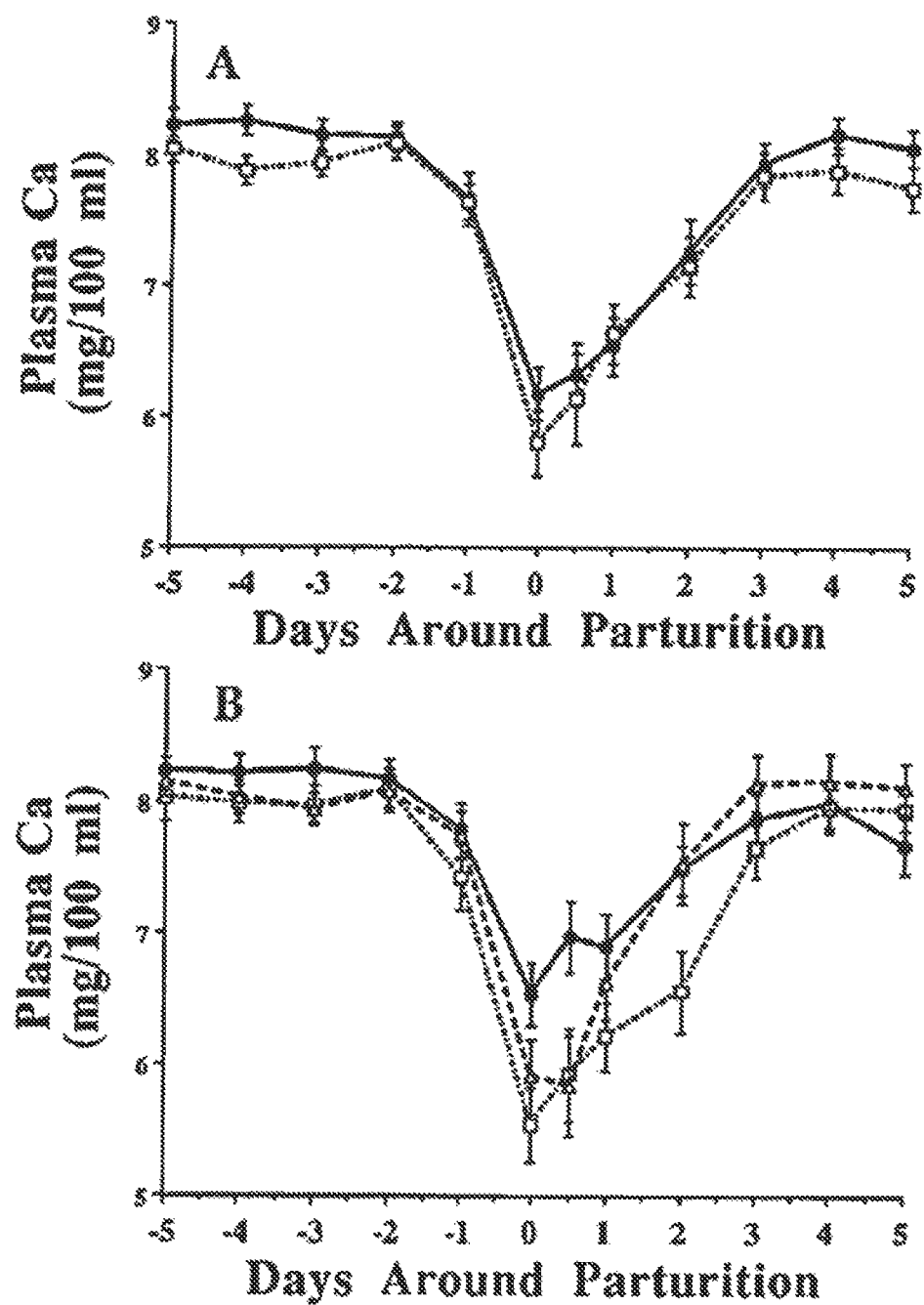

FIG. 8 depicts the course of plasma calcium around calving in untreated cows.

Figure 9:
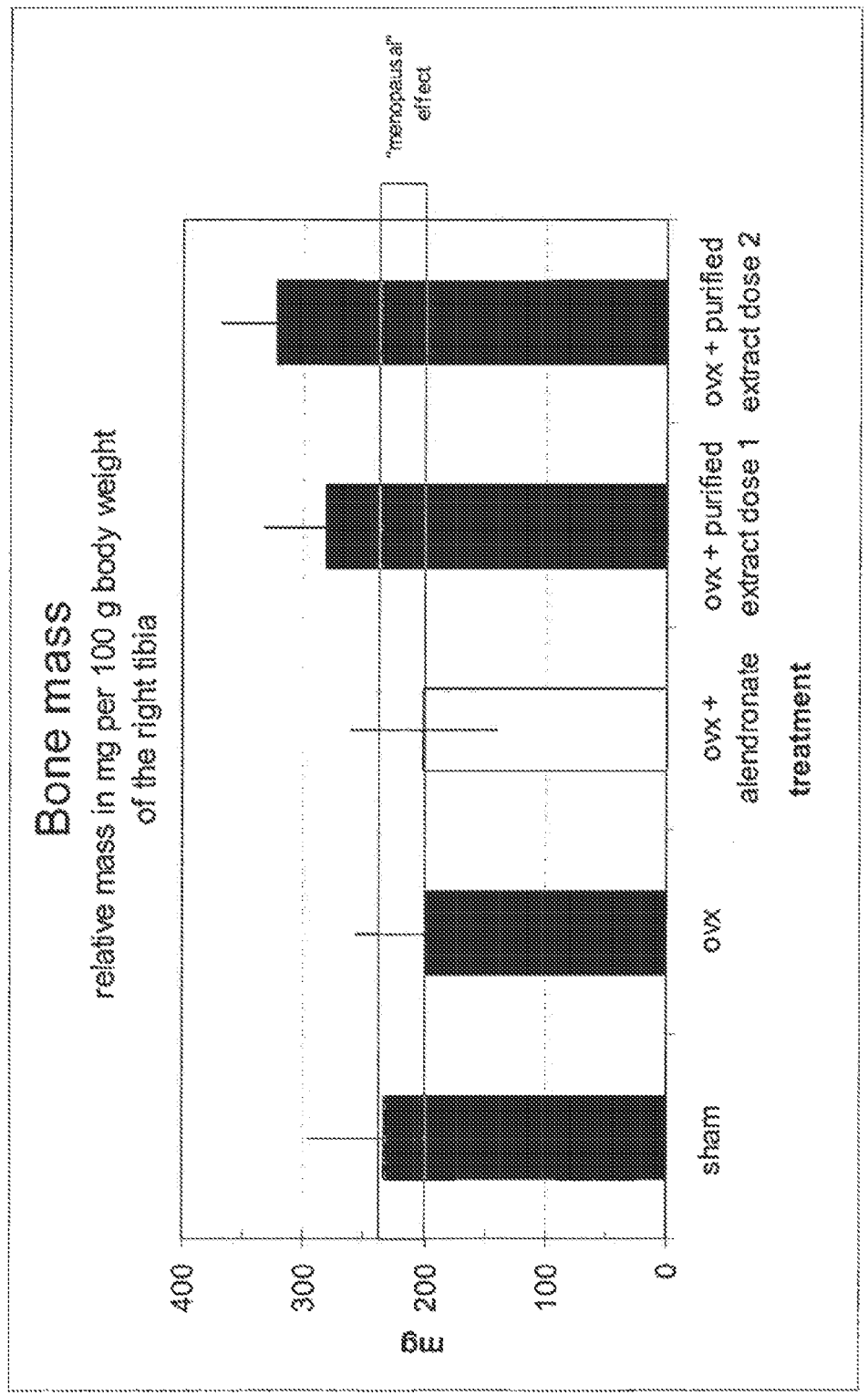

FIG. 9 shows the bone mass of the right tibia after 6 months of treatment in the rat model for osteoporosis (see also Experiment 4). As can be seen, treatment with the composition of the invention did not only prevent ovariectomy-induced bone-loss, the composition increased bone mass in tibia over the sham-operated controls.

EXAMPLES

The following Examples are intended to illustrate the invention further. They are not intended to limit the subject matter of the invention thereto.

Example 1

Extraction

From the published extraction methods for *Solanum glaucophyllum* the extraction with chloroform-methanol was the most efficient procedure, however, the method is not usable for larger volumes and involving toxic reagents. The other published extraction method with water yields lower vitamin D activity and is therefore also inferior to the method of the present invention. In contrast, the present invention provides a technically optimized and ecological process for extraction and purification, preferably of dried leaves, of the plant *Solanum glaucophyllum* without the use of toxic reagents as described in Example 1 and with significantly higher yields.

Example 1A

Extraction on Laboratory Scale (Process L)

1 g ground dry leaves of *Solanum glaucophyllum* were submitted to an automated solvent extraction in a ASE-100 instrument (Dionex, USA). As solvents, following alcohol based solvents were used and masses were obtained (see Table 1):

| Solvent in v/v [1] | solvent ratio | Extract [mL/g plant raw material] | Yield [mg/g SG] [2] temperature 50° C. mean of 3 exps. | VDM [µg/g SG] [3] | Qu [mg/g SC] [4] | ratio VDM/Qu [µg/mg] bez auf SG einwaage | VDM [10(−3) µg/mg extract] = ppm | Qu [10(−6) mg/mg extract] = ppm | ef [5] | yf = VDM * [6] (Qu/1000) * ef |
|---|---|---|---|---|---|---|---|---|---|---|
| EtOH/H₂O | 100% | 23.1 | 88 | 1.3 | 1.0 | 1.3 | 14.5 | 12 | 1 | 0.2 |
| EtOH/H₂O | 85% | 22.2 | 197 | 8.2 | 6.4 | 1.3 | 41.8 | 33 | 1 | 1.4 |
| EtOH/H₂O | 75% | 21.8 | 247 | 20.1 | 8.5 | 2.4 | 81.1 | 34 | 1 | 2.8 |
| EtOH/H₂O | 65% | 22.3 | 311 | 23.1 | 8.8 | 2.6 | 74.3 | 28 | 2 | 4.2 |
| EtOH/H₂O | 50% | 22.1 | 352 | 20.7 | 9.1 | 2.3 | 58.7 | 26 | 2 | 3.0 |
| EtOH/H₂O | 35% | 22.3 | 313 | 20.6 | 7.3 | 2.8 | 65.6 | 23 | 2 | 3.1 |
| EtOH/H₂O | 25% | 24.0 | 371 | 24.6 | 8.8 | 2.8 | 66.3 | 24 | 2 | 3.4 |
| EtOH/H₂O | 0% | 23.3 | 315 | 16.8 | 5.8 | 2.9 | 53.5 | 19 | 1 | 1.0 |
| MeOH | 100% | 23.0 | 189 | 16.6 | 6.2 | 2.7 | 88.0 | 33 | 1 | 2.9 |
| MeOH | 65% | 17.9 | 340 | 19.1 | 9.9 | 1.9 | 56.2 | 29 | 2 | 3.3 |
| MeOH | 25% | 18.6 | 354 | 19.8 | 9.1 | 2.2 | 55.8 | 26 | 1 | 1.4 |
| 2-Propanol | 100% | 17.7 | 124 | 2.1 | 2.2 | 1.0 | 17.1 | 18 | 1 | 0.3 |
| 2-Propanol | 65% | 17.9 | 326 | 19.1 | 6.3 | 3.0 | 58.4 | 19 | 2 | 2.3 |
| 2-Propanol | 25% | 18.0 | 363 | 17.5 | 4.9 | 3.6 | 48.2 | 13 | 1 | 0.6 |
| n-Butanol | 100% |  | 70 | 1.4 | 3.6 | 0.4 | 19.9 | 51 | 1 | 1.0 | extraction: 1) ASE-100 model of Diones Instruments, Olten Switzerland under the following conditions: 5 extraction cycles at a temperature of 50° C.
yield: 2) mg dry extract per g raw material
VDM: 3) VDM as analytically determined 1,25-Dihydroxyvitamin D3 assay after hydrolysis
Qu: 4) Quercetin-glycosides after acid hydrolysis according to Ph.Eur.
ef 5) empirical process factor
yf 6) weighed goodness of process, formula:

$$yf = VDM * (Qu/1000) * ef$$

The efficacy of the extraction was calculated by the following formula:

$$Yf = VDM(\text{extract}) \cdot [Qu(\text{extract})/1000] \cdot ef,$$

whereby the terms [VDM] and [Qu] are calculated per g extract. The factor [ef] weights empirical factors as costs, ecology and quality of the extract (e.g. solubility). As a result of laboratory experiments, the factor of goodness obtained is presented as graph in FIG. 4.

Figure 4:
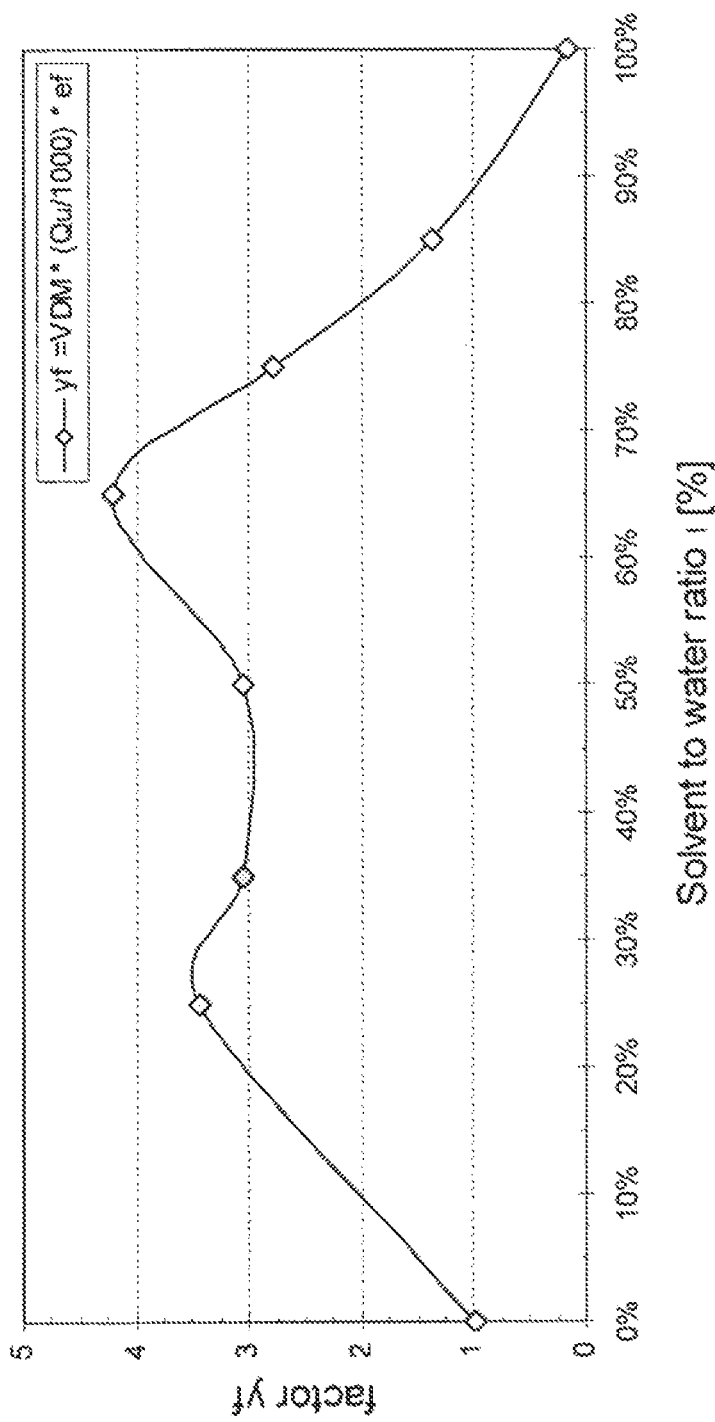
FIG. 4 shows the efficacy of the extraction calculated by the following formula.

The two peaks obtained from the graph in FIG. 4 according to the function above describe the merits of the process, which fulfil the criteria of the present invention and are satisfying and superior to known extraction methods. Extraction with other suitable and widely used solvents is less favourable for obtaining the optimal composition of product.

The peak at a solvent mixture of ethanol/water 25/75 is of special interest, because the dry extract possesses excellent water solubility, making such an extract suitable for any oral administration, e.g. via drinking water without the need to apply emulsifiers (as usual for the fat-soluble vitamins). The extract obtained with ethanol/water 65/35 has an lower water-solubility and may be used in, e.g. water insoluble formulations, e.g. when using emulsifiers, but also in other forms, such as tablets, capsules, etc., without the need of emulsifiers.

As a result of the experiments the efficacy of extraction yf greater than 3 is satisfying and superior to known extraction methods and fulfills the criteria of the present invention. Extraction with other suitable and widely used solvents is less favorable for obtaining the optimal composition of product.

The data obtained from purification of the extract obtained from laboratory process EL are as follows:

| | | mass g | content ppm | product [m*c] | mass yield k/k | purification factor VDM | yield % |
|---|---|---|---|---|---|---|---|
| Process EL EtOH/H$_2$O: 25/75 | | | | | | | |
| Raw material | in | 1 | 18 | 18 | — | — | |
| Extract | out | 0.371 | 47 | 17 | 0.37 | 2.6 | 97% |

Example 1B

Extraction Industrial Scale (i) Process EP 1000 kg dry leaves of *Solanum glaucophyllum* (5-15% water content) were extracted with 15-30,000 liters (preferably 25,000) of a 25-75 percent ethanol-water (w/w) mixture, which contained 0.1% ascorbic acid as stabilizer. Percolation was performed in 4 cyclically filled vessels at 55° C. for 24 hours per cycle in a state-of-the-art plant at a flow rate of 1.000 liter/hour. The pH of the received liquid phase was controlled and eventually adjusted to pH 5.5-6.5 by the addition of acetic acid. The obtained extract was collected and concentrated under vacuum to a content of 35% non-volatile matter. A high temperature treatment was carried out as described above. The data obtained from purification of the extract obtained from process EP are as follows:

| | | Mass kg | content ppm | product [m*c] | mass yield kg/kg | purification factor VDM | yield % |
|---|---|---|---|---|---|---|---|
| Process EP EtOH/H$_2$O: 25/75 | | | | | | | |
| Raw material | in | 3308 | 28 | 92'624 | — | — | |
| Extract | out | 933 | 76 | 70'908 | 0.28 | 2.7 | 77% |

(ii) Process EM

Instead of percolating a macerization process can also be used. Therefore, 1000 kg of dry leaves were filled in an appropriate stainless steel reactor provided with a mixer and a double jacket heating system. 9,000 Liter of ethanol-water (40-80% w/w, which may contain 0.1% ascorbic acid) were added. The mixture was heated to 40-75° C. (preferably 55) for 6-48 hours (preferable 24) under stirring followed by a liquid/solid separation in a filter press. The isolated leaves were extracted a second time in the same procedure using 8,000 Liter of solvent mixture.

The extract was filtered, the pH adjusted to 5.5-6.5 with acetic acid and concentrated in a two step vacuum evaporation unit to a content of 25-50% non-volatile matter. A high temperature treatment was carried out as described above. The data obtained from process EM are as follows:

| | | Mass kg | content ppm | product [m*c] | mass yield kg/kg | purification factor VDM | yield % |
|---|---|---|---|---|---|---|---|
| Process EM EtOH/H$_2$O: 25/75 | | | | | | | |
| Raw material | in | 200 | 26 | 5'200 | — | — | |
| Extract | out | 69.2 | 67 | 4'702 | 0.35 | 2.6 | 90% |

(iii) Processes EP+EM

Both concentrated extracts from (i) and (ii) (Processes EP and EM) were submitted to high temperature treatment as defined above and were used for the following step directly or were spray-dried, band dried or lyophilized.

Example 2

Purification

Example 2A

Purification on Laboratory Scale (Process PL)

Approximately 300 mg of a raw extract was dissolved in 1 ml water (or a solution of approximate 30% (w/v)) and applied onto a column of 9 ml bed volume, filled with the resin to be tested (the column is pre-conditioned according to its specifications). All solutions are applied with flow rate of approximately 0.3 bed volumes per minute. The column is washed with 3 bed volumes of water. Elution was performed with 3 bed volumes ethanol/water 95/05 (v/v) and the eluents are collected for analysis. The columns are regenerated with 3 bed volumes acetone. All 3 fractions, the aqueous wash (D105/1 A), the ethanol elute (D105/1 B) and the acetone regenerate (D105/1 C) was collected, evaporated to dryness and analysed. The column was conditioned with 2 bed volumes ethanol, followed with 2 bed volumes ethanol 50% and 4 bed volumes water before re-use.

Laboratory process purification (PL). the table describes all experimental data obtained in four runs:
Run 1: an extract obtained with solvent ethanol/water 25/75 (v/v) and column Amberlite XAD1180
Run 2: an extract obtained with solvent ethanol/water 25/75 (v/v) and column Amberlite XAD7HP
Run 3: an extract obtained with solvent ethanol/water 65/35 (v/v) and column Amberlite XAD1180
Run 4: an extract obtained with solvent ethanol/water 65/35 (v/v) and column Amberlite XAD7HP All Runs were collected in the 3 fractions: water wash (A), eluate (B) and regenerate (C) according to the method description above.

The data obtained from process PL are as follows:

The quotient VDM/Quercetin is higher when extraction was performed with ethanol/water 65/35 than 25/75 but mass yield was lower.

The eluate, obtained under the conditions applied, contains solely 1,25-dihydroxyvitamin $D_3$ glycosides and quercetin glycosides (as evidenced by HPTLC (FIG. 6, lane 4))

Under the present condition for elution with ethanol/water 96/04 (v/v) an optimum yield for VDE is obtained.

Example 2B

Purification in Industrial Scale (i) Industrial Purification Process (Example PF).

| fraction | Raw extract[1] | Appl. mg[2] | Insol mg[3] | Column type | mass mg/g rm[4] | VDM[5] μg/g rm | Qu[6] mg/g rm | mass yield % | VDM ppm in e[7] | VDM yield[8] | Qu mg/g in e[9] | Qu yield[10] | VDM/Qu [*10⁻³][11] |
|---|---|---|---|---|---|---|---|---|---|---|---|---|---|
| 1A (wash) | 25/75 | 329 | | Amberlite XAD1180 | 235 | 0.8 | 0.02 | 71% | 3 | | 0.1 | | |
| 1B (eluate) | " | | | | 54 | 14.3 | 5.36 | 16% | 266 | 78% | 99.7 | 99% | 2.67 |
| 1C (regenerate) | " | | | | 21 | 1.5 | 0.02 | 6% | 73 | | 1.0 | | |
| 2A (wash) | 25/75 | 354 | | Amberlite XAD7HP | 251 | 0.9 | 0.01 | 71% | 4 | | 0.0 | | |
| 2B (eluate) | " | | | | 88 | 19.5 | 7.35 | 25% | 221 | 97% | 83.3 | 95 | 2.65 |
| 2C (regenerate) | " | | | | 36 | 0.1 | 0.16 | 10% | 3 | | 4.6 | | |
| 3A (wash) | 65/35 | 313 | 35 | Amberlite XAD1180 | 193 | 0.9 | 0.05 | 69% | 5 | | 0.2 | | |
| 3B (eluate) | " | | | | 66 | 19 | 6.69 | 24% | 287 | 77% | 101 | 93% | 2.84 |
| 3C (regenerate) | " | | | | 18 | 1.5 | 0.13 | 7% | 82 | | 6.8 | | |
| 4A (wash) | 65/35 | 349 | 29 | Amberlite XAD7HP | 195 | 0.4 | 0.01 | 61% | 2 | | 0.0 | | |
| 4B (eluate) | " | | | | 87 | 21.8 | 6.55 | 25% | 250 | 98% | 75.1 | 86% | 3.33 |
| 4C (regenerate) | " | | | | 23 | 0.1 | 0.29 | 7% | 4 | | 12.4 | | |

[1]Raw extract obtained with solvent mixture ethanol/water
[2]Amount raw extract dissolved in 1 ml water applied onto column
[3]the raw extract from ethanol/water 65/25 is not complete soluble in 1 mL water, the remaining insoluble part was weighed back
[4]extract mass as mg per gram raw material (dry Solanum glaucophyllum leaves).
[5]VDM as analytically determined total 1,25-dihydroxyvitamin D
[6]Qu as analytically determined quercetin after hydrolysis
[7]VDM in ppm (μg/mg) purified extract obtained)
[8]Yield of VDM in eluate per applied material to column
[9]Quercetin in mg/mg purified extract obtained
[10]Yield of quercetin in eluate per applied material to column
[11]VDM/Qu quotient in μg 1,25-dihydroxyvitamin D per mg analytical determined quercetin Discussion:

Purification on Amberlite XAD-1180 and Amberlite XAD-7HP is superior to chromatography on silica gel and Sephadex material as described in literature (data not shown).

Chromatography of the raw extract from *Solanum glaucophyllum* on Amberlite XAD-1180 yields a product of higher solubility and of lighter color. However chromatography on Amberlite XAD-7PH yields higher mass and higher VDM, whereas quercetin yield was slightly lower. Purity was equal with both resins.

0.4 kg of a raw extract (derivable from process EP (Example 1B OM was applied onto an Amberlite XAD-7HP column of 4 L volume. 64 g purified product was obtained with a content of 229 ppm vitamin D metabolite (VDM, analytically determined as 1,25-dihydroxyvitamin $D_3$) and 17.7% flavonols (determined as quercetin after acid hydrolysis). The purified product contains solely quercetin as flavonol component after hydrolysis.

The data obtained from process PF are as follows:

| | | mass kg | VDM ppm | Qu mg/g | product [m*c] | Process PF Amberlite XAD-7HP mass yield kg/kg | purification factor VDM | purification factor Qu | Yield 1) % |
|---|---|---|---|---|---|---|---|---|---|
| Raw extract 2) | in | 0.400 | 46 | 17 | 18.4 | — | — | — | — |
| Extract 1) | out | 0.064 | 229 | 176.8 | 15 | 0.48 | 5.0 | 10.4 | 80% |

1) mass yield after drying
2) raw extract was applied as a 10% aqueous solution onto the column (ii) Industrial Purification Process (Example PS)

9 liter of a 30% raw extract solution (derivable from process EM (Example 1B (ii))) was applied onto a Amberlite XAD-1180 column of 35 L volume. 575 g purified product was obtained with a content of 322 ppm vitamin D metabolite (VDM, analytically determined as 1,25-dihydroxyvitamin $D_3$) and 15.9% flavonols (determined as quercetin after acid hydrolysis). The purified product contains solely quercetin as flavonol component after hydrolysis.

The data obtained from process PS are as follows:

| | | mass kg | VDM ppm | Qu mg/g | product [m*c] | mass yield kg/kg | purification factor VDM | purification factor Qu | Yield 1) % |
|---|---|---|---|---|---|---|---|---|---|
| Raw extract 2) | in | 9 | 29 | 17 | 261 | — | — | — | |
| Extract 1) | out | 0.575 | 322 | 158.9 | 185 | 0.19 | 11.1 | 9.3 | 71% |

Process PS
Amberlite XAD-1180, mean of 6 experiments

1) After drying
2) A solution of 9 l containing 30% dry matter was applied onto 35 l resin The inventive enriched plant extract obtained with either purification step (i) or (ii) above is a composition with a standardized content of the active vitamin $D_3$ metabolite 1,25-dihydroxyvitamin $D_3$ in glycosidically bound form and an optimum and uniform content of the bone active flavonol quercetin, also present in glycosidically bound form.

Example 3

Characterization of the Properties of the Enriched Plant Extract (i) Characterization of the Enriched Plant Extract in General:

The obtained preparation was analyzed and is characterized in terms of its active components, inactive ingredients and the absence of toxic components, wherein the product has been optimized for a minimum content of toxic components and minimum browning/discolorization during the production steps. Particularly, the enriched plant extract, i.e. the product obtained by the above described preparation (Examples 1 and 2) was characterized by the following properties:

| | |
|---|---|
| Active content as 1,25-dihydroxyvitamin $D_3$ | >300 µg/g[1)] |
| Active content as quercetin | >150 mg/g |
| Inactive content as carbohydrates (after acid hydrolysis)[2)] | <750 mg/g |
| Inactive content as protein[3)] | <20 mg/g |
| Inactive content as fat[4)] | <20 mg/g |
| Inactive content as plant acids, pigments and phytosterols | <20 mg/g |
| Inactive content as inorganic matter | <60 mg/g |
| Toxic content as alkaloids | <0.5 mg/g |
| Toxic content as residues of heavy metals and pesticides | According to Ph. Eur. |
| Has a quotient of active Vitamin D (expressed as 1,25-dihydroxyvitamin $D_3$) to active flavonol (expressed as quercetin) | $1-5 * 10^{-3}$ |

Figure 1:
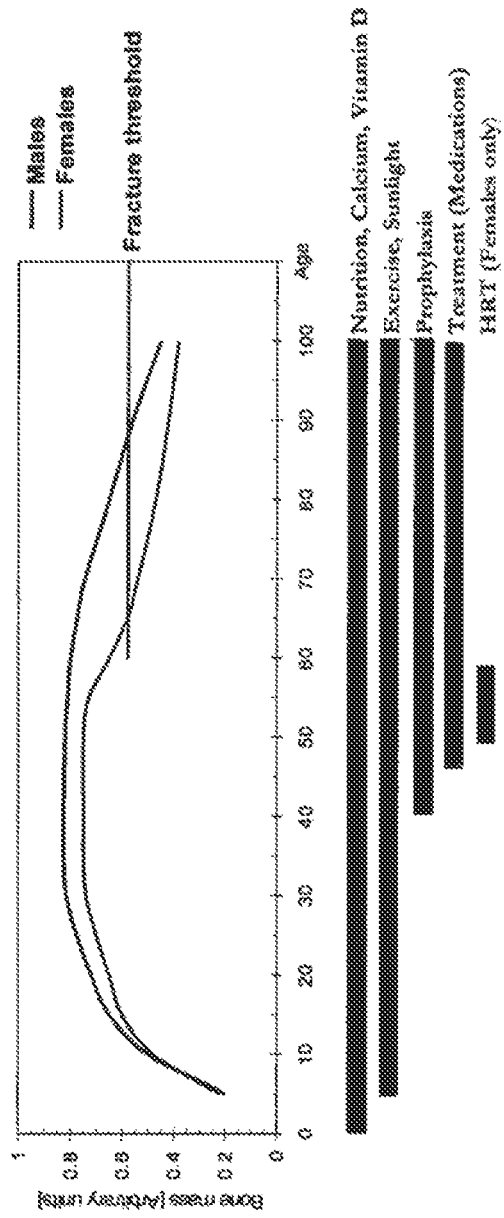
FIG. 1 shows the measures influencing bone mass in the context of Osteoporosis between males and females. As can be seen, nutrition is the most important factor over the entire life span. Specific medication plays an important role in patients with an age of more than 45 years.
Figure 2:
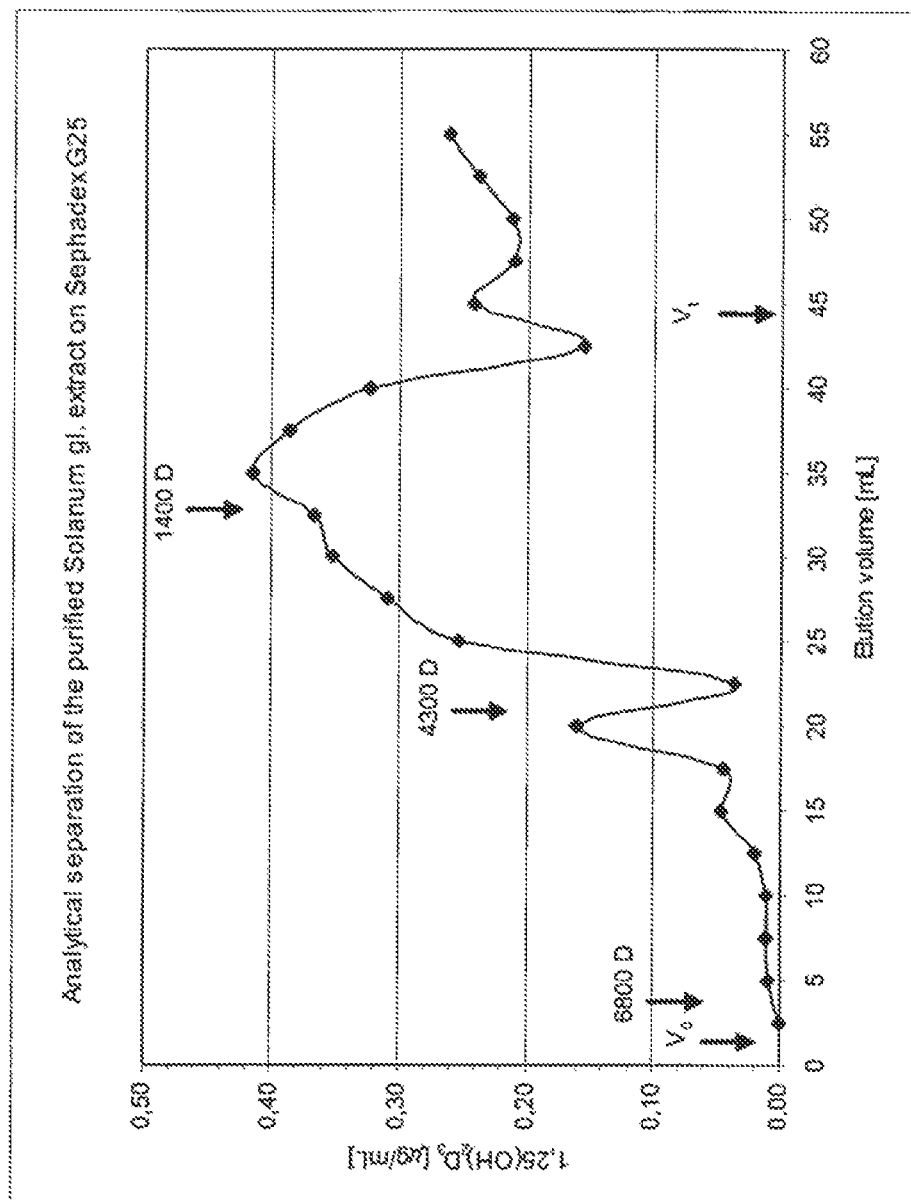
FIG. 2 shows the characterization of the inventive enriched plant extract, using a chromatographic separation of the purified extract on an analytical Sephadex G25 column. Aliquots of the fraction were applied to hydrolysis and assayed for 1,25-dihydroxyvitamin $D_3$ Water-soluble polystyrene with 1400, 4300 and 6800 Daltons was used a mass marker. As can be seen in FIG. 2, 1,25-dihydroxyvitamin $D_3$ represents a main component of the inventive enriched plant extract.
Figure 3:
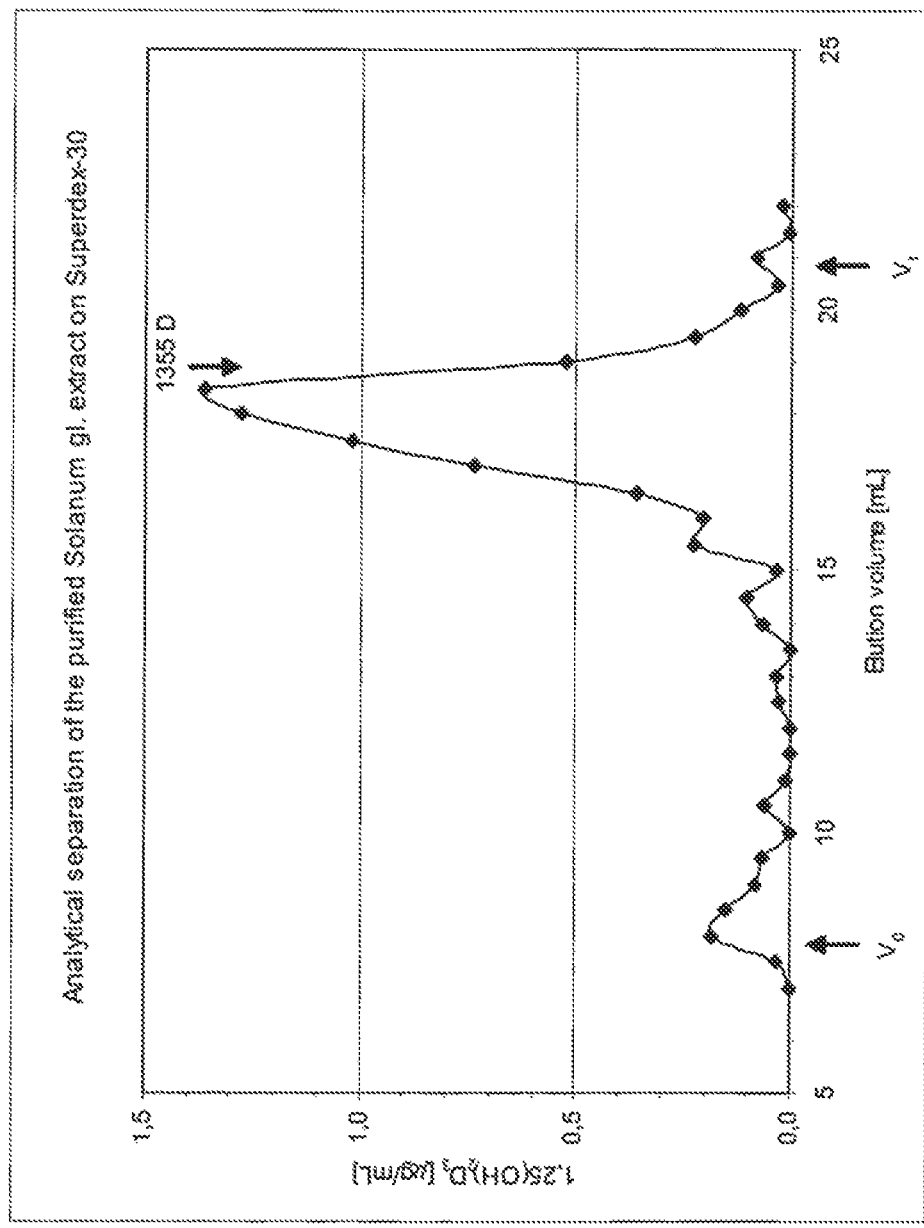
FIG. 3 shows the characterization of the inventive enriched plant extract, using a different chromatographic separation of the purified extract on an analytical Superdex-30 column. Aliquots of the fraction were applied to hydrolysis and assayed for 1,25-dihydroxyvitamin $D_3$. Cobalamin with a molecular mass of 1355 Daltons was used a mass marker. As can be also seen in FIG. 3, 125-dihydroxyvitamin $D_3$ represents a main component of the inventive enriched plant extract.

> greater than
< less than
[1)] at least 15 times higher than content in raw material
[2)] determination of reducing carbohydrates (Lit)
[3)] precipitation in 10% trichloroacetic acid
[4)] extraction with hexane (ii) Characterization by Vitamin D Active Components The composition, i.e. the inventive enriched plant extract prepared above, is further characterized by the presence of the vitamin D active components as 1,25-dihydroxyvitamin $D_3$ glycosides with a molar mass distribution of 596.8 (416.6+180.2) to 4500 Dalton (A chromatographic separation of the purified extract on an analytical Sephadex G25 column is shown in FIG. 2. Aliquots of the fraction were applied to hydrolysis and assayed for 1,25-dihydroxyvitamin $D_3$. Water-soluble polystyrene with 1400, 4300 and 6800 Daltons was used a mass marker. A chromatographic separation of the purified extract on an analytical Superdex-30 column is shown in FIG. 3. Aliquots of the fraction were applied to hydrolysis and assayed for 1,25-dihydroxyvitamin $D_3$. Cobalamin with a molecular mass of 1355 Daltons was used a mass marker). Furthermore, the composition is characterized by the presence of 1,25-dihydroxyvitamin $D_3$-1β-glucopyranoside (see also FIG. 5) as revealed by LC-MS-, UV-, $^1$H-NMR and $^{13}$C-NMR spectra.

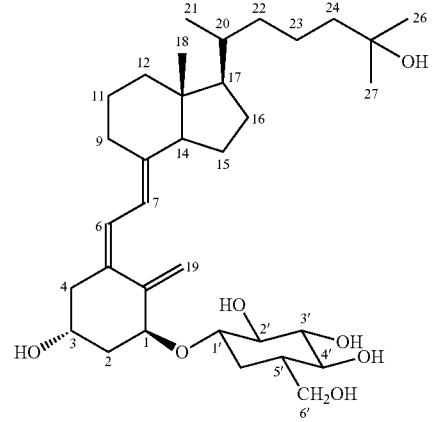 [SMILES: C=C1/C(=C\C=C2/CCC[C@@]3(C)C2CC[C@@H]3C(C)CCCC(C)(C)O)C[C@@H](O)C[C@@H]1OC1CC(CO)C(O)C(O)C1O]

A further characteristic of the inventive enriched plant extract is the absence of free 1,25-dihydroxyvitamin $D_3$ and 25-hydroxyvitamin $D_3$.

The analytical data of the main compound 1,25-dihydroxyvitamin $D_3$-1β-glucopyranoside are as follows:

LC-MS-spectrum (POS TIME=7.787:8.041):
m/z-=543 $[M+H-2H_2O]^+$, 399 $[M+H-Glu]^+$, 381 $[M+H-H_2O-Glu]^+$, 363 $[M+H-2H_2O-Glu]^+$ (see; CTL: m/z=399 $[M+H\ H_2O]^+$, 381 $[M+H-2H_2O]^+$, 363 $[M+H-3H_2O]^+$,
(CTL=calcitriol);
Molecular Mass (ESI-TOF):

$C_{33}H_{54}O_8$ m/z $[M + Na^+]$:  calc. 601.3736
$C_{66}H_{108}O_{16}$ m/z $[M + Nal^+]$:  found: 601.3711  Difference: 4.2 ppm calc. 1179.7530
found: 1179.7520 Difference: −0.8 ppm UV-Spectrum:

The UV-spectra shows two maxima which are only observed at CTL-compounds with groups on the C1—O position.

UV [MeOH/H$_2$O (9:1)]:$^2{}_{max}$=244.71.

$^1$H-NMR-spectrum (400 MHz, CDCl$_3$, 40° C.):

δ[ppm]=0.55 (s, 3H, 18), 0.94 (d, $^3$] (21.20)=6.4 Hz, 3H, 21), 1.22 (s, 6H, 26/27), 3.30 (dd, $^3$](2', 3')=9.2 Hz, $^3$] (2', 1')=7.6 Hz, 1H, 2'), 3.38 (m, 1H, 5'), 3.48 (dd, $^3$](4', 3')=9.2 Hz, $^3$](4', 5')=8.8 Hz, 1H, 4' or 3'), 3.59 (dd, $^3$](3', 2')=9.2 Hz; $^3$](3, 4')=9.2 Hz; 1H, 3' or 4'), 3.83 (dd, $^2$](6b', 6a')−= 12.0 Hz, $^3$](6b', 5')=4.8 Hz, 1H, 6b'), 3.93 (dd, $^2$](6a', 6b')=11.6 Hz, $^3$](6a', 5')=3.6 Hz, 1H, 6a'), 4.17 (m, $^3$](3α, 4β)=5.6 Hz, $^3$](3α, 4α)=3.6 Hz, 1H, 3α), 4.36 (d, $^3$J(1', 2')=7.6 Hz, 1H, 1'), 4.45 (t, $^3$J(1β, 2)=−4.0 Hz, 1H, 1β), 5.15 (d, $^2$J(19E, 19Z)=2.0 Hz, 1H, 19E), 5.30 (d, J$^2$)(19Z, 19E)= 1.6 Hz, 1H, 19Z), 5.98 (d, $^3$J(7, 6)=11.6 Hz, 1H, 7), 6.40 (d, $^3$)J(6, 7)=11.2 Hz, 1H, 6).

$^{13}$C-NMR Spectrum (CDCl$_3$):

δ[ppm]=12.1 (18), 18.8 (21), 29.2 (26/27), 62.5 (6'), 99.1 (1β), 117.1 (19E), 117.1 (19Z).

Thus, the presence of 1,25-dihydroxyvitamin D$_3$-1β-glucopyranoside was unambiguously identified.

(iii) Characterization by Plant Flavonols

The composition, i.e. the inventive enriched plant extract prepared above, is additionally characterized by the presence of only one bioactive flavonoid, the flavonol quercetin in glycosidic form. The composition of the quercetin glycosides is given in Table 2 and characterized as fingerprint after high performance thin layer chromatography according to FIG. 6. High performance thin layer chromatographic characterization was carried out using the obtained preparation and a comparison with standards and a gingko and a hawthorn extract (see Example 3 (iii)). The conditions were as follows:

| plates: | silicagel G with UV-Indicator 10 × 10 cm Merck(Camag AG, Muttenz Switzerland) |
|---|---|
| Solvent: | ethyl acetate/formic acid/acetic acid/water (100 + 11 + 11 + 26). 45 minutes pre-condition, running time 45 minutes; |
| Detection | Naturstoff-Reagent (Camag AG, Muttenz Switzerland); |
| Application: | Lane 1: quercetin (rf 0.88; 0.56 µg); hyperosid (rf 0.55; 1.25 µg); chlorogenic acid (rf 0.42; 1.2 µg); rutin (rf 0.37; 0.73 µg) (lane contains reference standard from Fluka AG, Buchs Switzerland); |
| | Lane 2: kaempferol (rf 0.90; 0.25 µg); isoquercitrin (rf 0.57; 1.25 µg); hyperosid (rf 0.54; 1.25 µg); (lane contains reference standard from Fluka AG, Buchs Switzerland); |
| | Lane 3: caffeic acid (rf 0.82; 0.1 µg); isoquercitrin (rf 0.57; 1.25 fig) (lane contains reference standard from Fluka AG, Buchs Switzerland); |
| | Lane 4: purified extract (Batch 1; 41 fig), 41 µg of the purified enriched plant extract of the present invention has been applied. Quercetin, quercetin glycosides and ubiquitous secondary plant extracts, including caffeic acid and chlorogenic acid can be separated (see FIG. 6); |
| | Lane 5: purified extract (Batch 2; 41 µg), Likewise, 41 µg of the purified enriched plant extract of the present invention has been applied. Quercetin, quercetin glycosides and ubiquitous secondary plant extracts, including caffeic acid and chlorogenic acid can be separated (see FIG. 6); Lanes 4 and 5 show a slight batch-to-batch difference; |
| | Lane 6: ginkgo biloba extract (commercial product; 10 µl) (commercial ginkgo biloba extract (Ceres AG, Switzerland)); |
| | Lane 7: hawthorn extract (commercial product; 201 µg) (commercial hawthorn extract (Zeller AG, Romanshorn, Switzerland). Both extracts of lanes 6 and 7 are of a distinct different composition.); |
| | Lane 8: Standards identical to lane 1 (Fluka AG, Buchs Switzerland); |
| | Lane 9: purified comparative extract according to the art (chromatography on Sephadex G-10) (comparative sample of an extract purified on a Sephadex G10 column. Despite of the high enrichment rate of the vitamin D activity (2000 µg/g) virtually no flavonols are present). |

The analysis of the high performance thin layer chromatographic characterization lead to following results (see Table 2):

TABLE 2

Flavonol content of inventive enriched plant extract

| Quercetin glycosides | mg/g |
|---|---|
| Apiosyl rutin | 50-100 |
| Rutin | 120-200 |
| Other quercetin oligosaccharides | 5-50 |
| Hyperoside | 5-20 |
| Other quercetin monoglycosides | 10-50 |
| Quercetin | 2-50 |
| Kaempherol | <20 |

It is to be mentioned, that the purification by chromatography on Sephadex resins yields a product of high 1,25-dihydroxyvitamin D$_3$ content, however by the virtual absence of flavonols as seen in lane 9 of FIG. 5.

Example 3

Experiments Testing the Biological Action of the Inventive Enriched Plant Extract N Assessment of the Vitamin D Activity by Means of a Bioassay in Japanese Quails (Experiment 1

From Rambeck et al. (see Rambeck et al, Ann. Nutr. Metab. 30, 9-14, (1986)) it is known that the quail egg shell assay is used as a simple bioassay to assess Vitamin D activity. According to this assay, Japanese quails (Coturnix japonica) of egg laying age and selected for a laying performance of >80% were set on a Vitamin D-deficient diet containing all other nutrients in optimal amounts. After approximately 8 days, the laying performance as the most sensitive marker dropped below 10%. Then, the test animals were randomly divided into groups of 10 animals and the diet was changed to the same diet, but supplemented with the substance to be tested. Laying performance was monitored for 21 days together with other markers of vitamin D-metabolism, such as alkaline phosphatase and calcium in plasma.

In Experiment 1 three groups of quails received 100, 200 and 400 international units of vitamin D$_3$ per kg feed, 5 groups received 2, 8, 32, 128 and 514 mg/kg purified plant extract and one group was given synthetic 1, 25-Dihydroxyvitamin D$_3$ (1 µg/kg feed) and another group received ground dried leaves of Solanum glaucophyllum (1000 mg/kg feed).

TABLE 3

Eggshell weight (ESW) in g per day and animal as parameter for the vitamin D activity in the Japanese quail bioassay

| Test substance and given dose | dose | Units per kg feed | ESW [g] days 5-21 | ±SD % |
|---|---|---|---|---|
| Vitamin $D_3$ | 100 | IUD | 0.231 | 0.133 |
| Vitamin $D_3$ | 200 | " | 0.434 | 0.183 |
| Vitamin $D_3$ | 400 | " | 0.738 | 0.169 |
| Purified extract | 2 | mg | 0.017 | 0.029 |
| Purified extract | 8 | " | 0.187 | 0.164 |
| Purified extract | 32 | " | 0.687 | 0.152 |
| Purified extract | 128 | " | 0.802 | 0.071 |
| Purified extract | 512 | " | 0.782 | 0.176 |
| Synthetic $1,25(OH)_2D_3$ | 1 | µg | 0.502 | 0.170 |
| Solanum glaucophyllum leaves | 1000 | mg | 0.361 | 0.156 |

Evaluation by probit analysis of the eggshell weights showed a vitamin $D_3$ activity of the purified extract of about 10,000 IUD/g, whereas in the leaves of Solanum glaucophyllum a vitamin $D_3$ activity of about 200 IUD/g has been found (1 International Unit (IU) of Vitamin D (IUD) is the biological equivalent of 0.025 µg cholecalciferol/ergocalciferol). Therefore, the obtained composition has a 50 time higher vitamin D activity than the basic raw material.

In addition to the determination of the vitamin D-activity, the experiment revealed a good acceptance of the purified extract over a wide dosage range. For the synthetic 1,25-dihydroxyvitamin $D_3$ a therapeutic window of 2 to 5 is found in chickens (see Rambeck et al, supra) whereas the purified extract was well tolerated over a dosage range from 32 mg/kg feed (beginning of effect) up to 512 mg/kg feed without showing a decline of the egg laying performance (ESW in Table 3).

Moreover, the onset of egg laying after the beginning of the treatment with the purified extract of Solanum glaucophyllum was faster than with vitamin $D_3$ as can be estimated by the time by which laying performance passed 50%. By treatment with the purified extract, time is 24-48 hours, whereas by treatment with vitamin $D_3$ is 48-72 hours.

A further finding is the significant increase of the weight of the eggs in the groups given the purified extract compared with the standard group receiving 400 IUD/kg feed as shown in Table 4 below.

TABLE 4

The average egg weight between day 1 and 21 collected in the Japanese quail bioassay

| Test substance and given dose | Egg weight g | SD* g | % | P** |
|---|---|---|---|---|
| Vitamin D3 100 IUD/kg feed | 9.61 | 0.74 | 90% | |
| Vitamin D3 200 IUD/kg feed | 10.40 | 0.60 | 97% | ns*** |
| Vitamin D3 400 IUD/kg feed | 10.70 | 0.71 | 1.00 | — |
| Purified extract 32 mg/kg feed | 11.23 | 0.77 | 105% | 0.034 |
| Purified extract 128 mg/kg feed | 11.27 | 0.67 | 105% | 0.007 |
| Purified extract 512 mg/kg feed | 11.39 | 0.81 | 106% | 0.007 |
| Synthetic 1,25(OH)2D3 1.0 µg/kg feed | 10.58 | 0.80 | 99% | ns*** |
| Solanum gl. leaves 1000 mg/kg feed | 10.50 | 0.56 | 98% | ns*** |

*standard deviation
**significance obtained by single sided ANOVA analysis
***not significant (ii) Broiler Experiment for Leg Anomalies (Experiment 2)

In experiment 2, male one-day old broiler chickens were fed a commercial diet containing 1,000 IUD/kg feed of vitamin $D_3$ ad libitum. A control group received the unsupplemented diet whereas in two other groups the diet was supplemented with 32 mg/kg and, respectively, 128 mg/kg of the purified extract corresponding to 4.3 resp. 76.8 µg 1,25-Dihydroxyvitamin $D_3$ (determined after in vitro hydrolysis of the extract). Table 5 shows the reduction of tibial dyschondroplasia (TD) and other leg anomalies in commercial broiler chickens after treatment with the inventive purified enriched plant extract from Solanum glaucophyllum.

TABLE 5

Treatment of tibial dyschondroplasia (TD) and other leg anomalies in commercial broiler chickens after day 14 of treatment.

| Test substance and given dose | Occurrence of TD (%) | Occurrence of other leg anomalies (%) | Healthy animals. (%) |
|---|---|---|---|
| Control group | 30.8 a | 26.9 a | 42.3 a |
| Purified extract 16 mg/kg | 6.9 *b | 0 b | 93.1 b |
| Purified extract 64 mg/kg | 0 *b | 3.2 b | 92.9 b |
| Synthetic 1,25-Dihydroxyvitamin $D_3$ 5 µg/kg (Positive control) | 3.55 *b | 3.55 b | 92.9 b |

*significance of treatment a vs. b p < 0.05

(iii) Activity in Preventing a Decline in Blood Calcium During Calving (Experiment 31

Milk fever is a metabolic disease in milk-producing animals around parturition, when reconstituting milk production depletes circulating calcium in mother blood. The endogenous calcium homeostasis is not able to mobilize enough calcium from food or bone to prevent a significant decrease in blood calcium. In certain cases the low calcium concentration induces muscle paresis. Today's treatment consists of applying large calcium doses around calving (see: The Merck Veterinary Manual, Parturient Paresis in Cows).

In the experiment pregnant cows were randomly distributed to two treatment regimes. One group received a commercial product containing 42 g calcium salts per application bolus. Four boli were given around calving according to the manufacturer's recommendation. The product of the present invention was given in one single dose of 5 g between 72 to 24 hours ante partum. A group without treatment was for ethical reasons not included; a per-parturient decrease in plasma calcium is well documented (see FIG. 7, Goff J P, Horst R I. J Dairy Sci. 1997 January; 80(1):176-86. Effects of the addition of potassium or sodium, but not calcium, to prepartum ratios on milk fever in dairy cows.).

As result, a single dose of the composition of the invention was able to prevent the decline in plasma calcium in the same manner as four applications of 43 g calcium around calving as seen in FIG. 7.

(iv) Activity in an Animal Model for Human Osteoporosis (Experiment 4)

The activity of the inventive enriched plant extract, which contained both active principles, i.e. 1,25-dihydroxyvitamin $D_3$ (as 1,25-dihydroxyvitamin $D_3$-1β-glucopyranoside) and the flavonoid quercetin, in a natural matrix has been tested in an ovariectomy-induced rat model for human menopausal osteoporosis, a preclinical model for osteoporosis to rats.

Ovariectomized female rats and sham operated litter mates of 120 g weight were obtained from Charles River Labs, L'Arbresle, France), and were separated into groups. After acclimatization they were fed with a control diet (groups sham and ovx) or the same diet containing the test products (sol and alendronate). Alendronate was tested as positive control in order to validate the experiment. Alendronate is introduced in human anti-osteoporosis therapy. During the experiment blood and urine was collected and markers of bone turnover and formation were assessed. After 6 months the experiment was terminated and bone ash and x-ray tomography of the tibiae measured.

An in vitro experiment to demonstrate the activity of the quercetin component of the present composition was done in bone cell culture with free quercetin and free 1,25-dihydroxyvitamin $D_3$ as positive controls.

As overall result, an unexpected strong effect was found for the inventive enriched plant composition, which may be explained by a synergistic action of the two active principles 1,25-dihydroxyvitamin $D_3$ and quercetin. Thus, treatment with the composition of the invention did not only prevent ovariectomy-induced bone-loss, the composition increased bone mass in tibia over the sham-operated controls as illustrated in FIG. 9.

The invention as claimed as follows:

1. A method of prevention or treatment of a bone mass reduction-related disease, the method comprising administering to a human or animal a pharmaceutical composition comprising an enriched plant extract from *Solanum glaucophyllum* obtained by a process comprising (a) forming an extract of plants or parts thereof from the *Solanum glaucophyllum* using an alcohol/water mixture having an alcohol/water ratio (%) of 75/25 to 25/75 (v/v), the alcohol selected from the group consisting of methanol, ethanol and isopropanol; and (b) purifying the extract obtained in step a) by b1) applying the extract obtained in step a) to a column comprising a non-ionic polymer resin selected from the group consisting of polystyrene, styrene-divinyl-benzene copolymers, acrylic ester polymers and polyphenolic resins; b2) washing the column with water; b3) eluting the enriched plant extract from the column; and b4) concentrating and/or drying the enriched plant extract.

2. The method of claim 1, wherein the enriched plant extract comprises at least 300 µg/g of 1,25-dihydroxyvitamin $D_3$.

3. The method of claim 1, wherein the enriched plant extract comprises more than 500 µg/g of 1,25-dihydroxyvitamin $D_3$.

4. The method of claim 1, wherein the enriched plant extract comprises more than 2000 µg/g of 1,25-dihydroxyvitamin $D_3$.

5. The method of claim 1, wherein the enriched plant extract comprises at least 100 mg/g of active quercetin glycosides.

6. The method of claim 1, wherein the enriched plant extract comprises at least 150 mg/g of active quercetin glycosides.

7. The method of claim 1, wherein the enriched plant extract comprises at least 200 mg/g of active quercetin glycosides.

8. The method of claim 1, wherein the enriched plant extract comprises no greater than 10 µg/g of alkaloids.

9. The method of claim 1, wherein the bone mass reduction-related disease comprises osteopenia.

10. The method of claim 1, wherein the bone mass reduction-related disease comprises osteoporosis.

11. The method of claim 1, wherein the human or animal has or is at risk of the bone mass reduction-related disease.

12. The method of claim 1, wherein the human or individual has osteopenia or osteoporosis.

* * * * *